US010159253B2

(12) United States Patent
Minturn

(10) Patent No.: US 10,159,253 B2
(45) Date of Patent: Dec. 25, 2018

(54) GREEN BIOCIDAL APPLICATION METHOD FOR THE PERFECT SILVER BULLET EXTERMINATORS

(71) Applicant: Paul Ash Minturn, La Jolla, CA (US)

(72) Inventor: Paul Ash Minturn, La Jolla, CA (US)

( * ) Notice: Subject to any disclaimer, the term of this patent is extended or adjusted under 35 U.S.C. 154(b) by 1065 days.

(21) Appl. No.: 14/499,492

(22) Filed: Sep. 29, 2014

(65) Prior Publication Data

US 2015/0030651 A1 Jan. 29, 2015

Related U.S. Application Data

(63) Continuation-in-part of application No. 13/333,528, filed on Dec. 21, 2011, now abandoned.

(51) Int. Cl.
*A61K 9/00* (2006.01)
*A01N 59/16* (2006.01)
*B82Y 5/00* (2011.01)

(52) U.S. Cl.

CPC ................ *A01N 59/16* (2013.01); *B82Y 5/00* (2013.01)

(58) Field of Classification Search

CPC ...................................................... A01N 59/16
See application file for complete search history.

(56) References Cited

U.S. PATENT DOCUMENTS

2010/0205709 A1* 8/2010 Grune .................... A01N 25/10 2/2.15
2016/0050935 A1* 2/2016 Furuzono ............... A01N 59/16 556/117

FOREIGN PATENT DOCUMENTS

RU 2403050 C2 * 11/2010
WO WO-2014163126 A1 * 10/2014 ............. A01N 59/16

OTHER PUBLICATIONS

English translation of RU-2403050-C2, Jan. 2018.*

* cited by examiner

*Primary Examiner* — Paul W Dickinson

(57) ABSTRACT

The present invention teaches a green non-toxic biocidal application technology that helps a person find, evaluate and produce the perfect pathogenic solution for safely exterminating unwanted, pathogenic and deadly organisms while contributing positively to regenerative and sustainable future ecosystems. This method enables the identification, selection and production of biocidal bioavailable pure silver particles and ions that are indefinitely clear, non-toxic, safe, ultra-small size=0.04-0.99 nanometers antimicrobial solutions for pure liquid or atomized implementation that are customized for completely annihilating specific targeted unwanted, pathogenic, deadly and/or disease-causing organisms. These custom formulated solutions can: (a) completely and safely annihilate many unwanted and/or pathogenic organisms that are contributing to dangerous and deadly pandemic conditions throughout the world, including: Gram Negative and Gram Positive Pathogenic Bacteria, and Gram Indeterminant Bacteria; (b) continually prevent or inhibit unwanted microbial and pathogenic growths; (c) save and/or keep things from decaying, decomposition, deterioration, spoiling, purification or fermentation; (d) safely resist or retard natural destructive processes; and, (e) be used as medical devices to significantly retard the carious destructive processes of nature with custom anti-microbial properties. There are nine (9) Restrictive Aspects that are integral, inter-dependent, inter-related and inseparable embodiments of this method and invention. The First Aspect is the primary restrictive embodiment requirement is a low-voltage colloidal silver generator. The Second Aspect stipulates that the silver nanoparticles must be suspended in a solution of super-distilled, less than 2 ppm, aqueous pure water medium. The Third Aspect, considered the most important of all, is the size that yields the best results usually ranges from 0.04 nm to 0.99 nm. The Fourth Aspect, second in importance, is the total ideal number of bioavailable single individual mini-silver particles and ion parts per million of individual single unattached bioavailable pure nano-sized (Continued)

silver particles. The Fifth Aspect constitutes of maintaining a consistently high biocidal ideal kill ratio that results in a lethal cold high-level annihilation agent that kills greater than ninety percent. The Sixth Aspect is an ideal death curve of the specific targeted organisms. The Seventh Aspect comprises the absolutely crystal clarity of the solutions which also includes conducting field studies. The Eighth Aspect is the capability of the biocidal solutions for selective genocide which are harmless to friendly probiotics. The Ninth Aspect means that the biocidal applicational does not produce any toxic waste, and contributes positively to a regenerative and sustainable future.

6 Claims, 3 Drawing Sheets

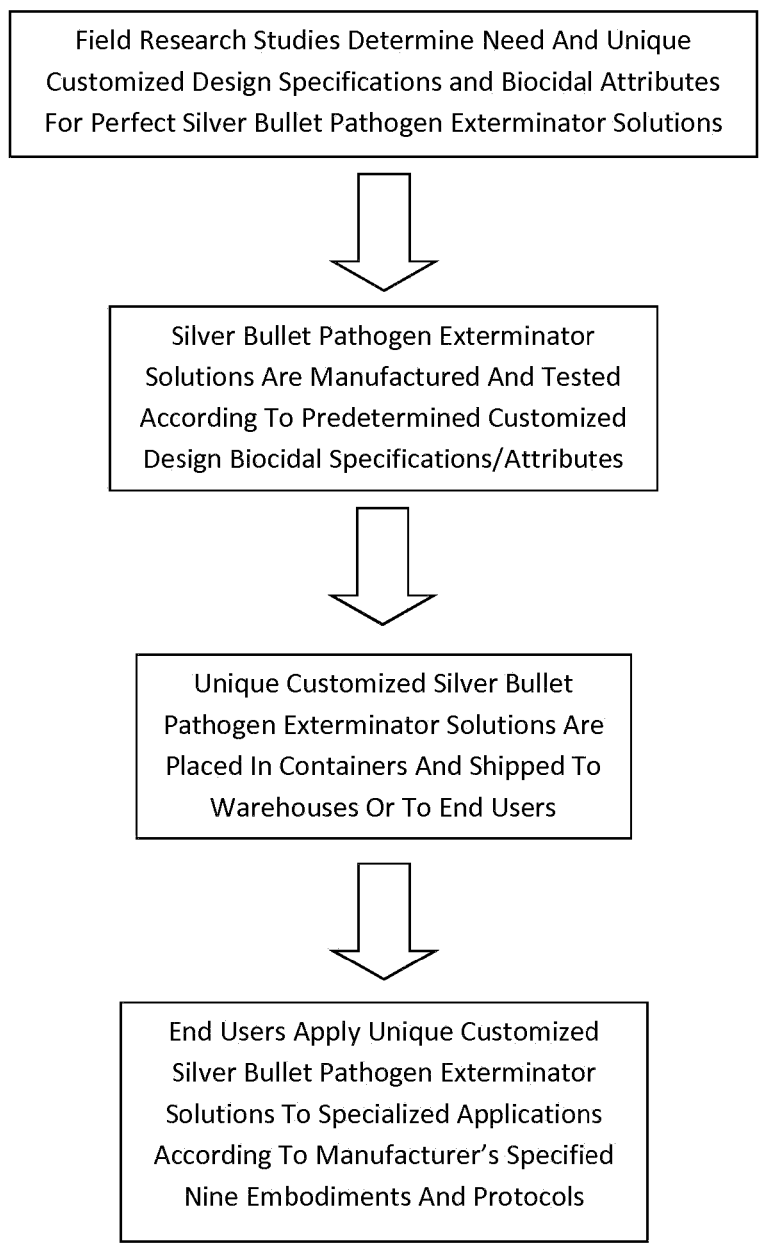

Figure 2

```
┌─────────────────────────────────────────────────────────┐
│ Controlled Field Tests Plus Lab Studies Determine The   │
│ Unique Customization Design Specifications and Attributes│
│ Of Perfect Silver Bullet Pathogen Exterminator Solutions│
└─────────────────────────────────────────────────────────┘
                           ⇩
┌─────────────────────────────────────────────────────────┐
│          Raw Materials Are Assembled And Lab Tested     │
└─────────────────────────────────────────────────────────┘
                           ⇩
┌─────────────────────────────────────────────────────────┐
│      Manufacturing Equipment Is Tested And Serviced As Needed │
└─────────────────────────────────────────────────────────┘
                           ⇩
┌─────────────────────────────────────────────────────────┐
│            Manufacturing Processes Prepare              │
│       Predetermined Unique Customized Perfect           │
│     Silver Bullet Pathogen Exterminator Solutions       │
└─────────────────────────────────────────────────────────┘
                           ⇩
┌─────────────────────────────────────────────────────────┐
│          Unique Customized Perfect Silver Bullet        │
│       Pathogen Exterminator Solutions Are Tested        │
│        For Quality Control And Then Placed In           │
│         Containers For Shipping To End Users            │
└─────────────────────────────────────────────────────────┘
```

GREEN BIOCIDAL APPLICATION METHOD FOR THE PERFECT SILVER BULLET EXTERMINATORS

BACKGROUND OF THE INVENTION

Technical Field

The present invention relates to a "Green" Applicational Method for Discovering, Evaluating, Producing, Implementing and Administering Customized Silver Bullet Solutions that can Safely Annihilate or Kill Unwanted and Pathogenic and Deadly Organisms. It also provides methods for saving and keeping things from decaying, decomposition, deterioration, spoiling, putrefication or fermentation through the safe reduction or elimination of the natural carious processes which result in unwanted infectious causing or contaminating chemical changes or in the growth of pathogenic bacteria or viruses. This invention avoids hazardous toxic chemicals, preservatives and embalming substances with safe "green-type" risk-free harmless specially formulated non-toxic, odorless, inexpensive, nano-scopic liquid preservative formulated solutions and embalming medical devices that have superior preservation, anti-microbial, decontaminating and embalming properties.

HISTORY PRECEDING THE INVENTION

Modern scientists are still trying to catch up and uncover the secrets of some of the ancient Old World preservation technologies for mummification that come from Egypt, China and Peru. These included resins, essential oils and numerous other secret embalming procedures that still baffle scientific researchers. It is possible that some of these ancient embalming artists knew about and took advantage of the widely known biocidal, anti-microbial, preservation, anti-pathogenic and safe-guarding properties of the tiny particles of the precious mineral known as silver. This noble metal has been in use since 4,000 BC (as a preservative and for a wide variety of healing purposes as well as for treating diseases and wounds). Eastern Persian records specifically mention the practice of placing water in silver vessels, and the ancient Babylonian and Greek civilizations were fully aware of silver's ability to preserve and disinfect.

According to the Greek historian, Herodotus, called the "Father of History", all the Persian kings, including Cyrus (who conquered Babylon), would only drink water from their own Choaspes River that flowed past the ancient capital of Susa. Wherever the kings went, a long train of four-wheeled mule wagons followed them transporting silver jars filled with boiled water from the river's waters. The water would remain fresh for years during the long campaigns.

At the height of the Roman Empire, silver compounds were used for medical treatment. During the Dark and Middle Ages, silver (in one form or another) was used to disinfect open wounds and keep both food and water from becoming contaminated by the Egyptians, Greeks, Romans and Phoenicians. Silver plates, bowls, utensils and silverware protected many of the wealthy by warding off diseases during the infamous plagues and pandemics. Members of royalty were often called "bluebloods," probably due to the silver content in their blood and the blueness of their skin. When eating, the royalty used almost exclusively silver plates, bowls, utensils and tableware. They essentially digested large particles of silver or silver oxides over an extended period of time, which likely created a permanent blue-grey discoloration of the skin (argyria), possibly due to the excessive silver deposits. Many of the pioneers of the "Old West" used silverware plus coins in their containers to prevent spoilage of their milk and water.

In the last century, scientists were beginning to develop more sophisticated forms of silver to kill germs. The USFDA has been regulating the uses of silver since 1913. In 1924, the first electro-colloidal silver was produced, resulting in tiny particles with positive charges that stayed in suspension. In March of 1978, *Science Digest* called colloidal silver the mightiest germ fighter known to medicine. The use of silver preparations in modern, conventional medicine has survived until this Modern Age. Among them are the uses of dilute silver nitrates in newborn babies' eyes to protect the infants from infection. Another important use is a silver based salve (called "Silvadine") that can be found in virtually every burn ward in North America to fight infection. Additionally, a patented silver coated nylon material (known as "Silvalon") was licensed by the FDA as an anti-microbial bandage.

Clearly, silver has historically been one of mankind's most reliable tools in preserving foods and water, in retarding infections and in supporting the immune system against various diseases, even before humans knew what caused these maladies. After reviewing 23 different water purification and preservation systems, NASA selected a silver-based system for the space shuttle, and Japan uses silver air purifiers. Ayurvedic physicians of India continue to use it for medicinal purposes to this day. Since the introduction of patented antibiotics for medicinal uses by the medical industries in the 1930s, the pharmaceutical industry has dominated anti-microbial science. Since that time, silver preparations and solutions have dramatically receded from general utilization until recently.

RESEARCH BEHIND THIS INVENTION

The combined expertise and backgrounds and relationships to any form or type of silver applications of the inventors of this invention include: actuarial sciences, longevity and medical research, sales/supply, electronic and computer technologies, archaeology, anthropology, scientific wellness, fitness and optimal health and infection control and sterile processing spanning over up to four decades.

Many years ago, with assistance from the world's first electron microscopist and several major university research departments, the inventor began a fascinating and independent investigation that included a variety of experiments evaluating the biocidal anti-microbial attributes and applications of tiny colloidal silver particles in non-toxic, safe "green-type" anti-germicidal systems/methods that created only non-hazardous waste, for the purpose of: (1) killing and exterminating unwanted and/or pathogenic organisms; (2) preventing unwanted bacterial or viral growth in a wide variety of applications; (3) healthful preservation of foods and drinks (without latent chemical or toxic side-effects); (4) retarding the natural decaying and spoiling processes in foods and beverages; (5) embalming (of bodies, organs and tissues); and, (6) preserving and safe-guarding against the customary ever-increasing exponential growth of pathogenic and deadly methylcillin resistant organisms in ordinary, sterile or polluted environments. It was noticed that the use of non-toxic, safe "green-type" tiny colloidal silver particles in suspension in pure water solutions appeared to have some of the same biocidal or preservative characteristics similar to standard toxic chemicals and preservatives. It was repeatedly observed that a wide variety of foods lasted longer without the usual spoilage when sprayed or soaked in these non-toxic, safe "green-type" small colloidal silver particles in suspension in pure water solutions.

It was also discovered that the longevity and usefulness of laboratory research specimens was greatly improved by similar exposure to the same non-toxic, safe "green-type" tiny colloidal silver particles in suspension in pure water solutions. Wanting more information, this inventor next supervised the precise application of specially formulated solutions of mini-nano-sized colloidal particles of pure silver to various "killer molds and fungi" commonly found in dark places in the moist and tropical Eastern and Western Coastal Areas of North, Central and South America. The lethal results of controlled tests/applications of these specially formulated suspended mini-nano-sized particles of pure silver solutions to these highly toxic molds and fungi was successful, and the inventor initiated some further research in controlled university laboratory tests on the application of various concentrations of mini-nano-sized colloidal particles of pure silver in stable solutions to selected pathogenic bacterial and viral organisms.

During the next few years, numerous private scientifically controlled laboratory and field tests were done to determine the optimal sispppm (single individual silver particle parts per million concentrations) of nano-sized colloidal particles of pure silver for the highest kill ratio combined with an ideal death curve when applied to these pathogenic organisms. Between 1996 and 2006, this leading-edge research was expanded with the help of Joseph Goodman, Ph.D., a highly published pioneering electron-microscope scientist at the University of California at San Francisco (UCSF). Dr. Goodman enjoyed a world-wide reputation as a brilliant mad scientist and a respected electron microscopist who had published important research papers on AIDS, Alzheimer's disease and other topics as a top honored university microbiologist. Dr. Goodman had a 60-year career as a respected Pediatric university professor and researcher at UCSF. Fortunately, much of the laboratory culturing of bacteria and viruses was done by kind supportive colleagues and staff who took a deep interest in this important "green" but controversial research. As the research continued, many grad students and faculty helped with the difficult task of capturing the fast microscopic lethal actions for electron microscopy evaluation of various concentrations (ppms) of silver formulations which killed only pathogens but had no negative effects on enzymes, flora, fauna or "good" probiotic bacteria.

Initially, the most common concentration of 10 ppm was first carefully analyzed. Other concentrations included 1, 5, 15, 20, 25, 40, 50, 100 and 200 ppms. These were also studied. However, the higher ppms (>10) seemed to reduce the desired kill ratios when exposed to the targeted bacteria or viruses. Perhaps this was an example of the mysterious "homeopathic phenomena" where minute doses of substances achieve more desirable outcomes (but with no negative side effects) than massive "allopathic" treatments that usually have serious to catastrophic unwanted side effects. In most tests, the highest kill ratio (>90%) was achieved by ppms from 1 to 6 (with 4.5 ppm being the most ideal). Larger colloidal silver particles (5-100 nanometers in size, often oxidized) were evaluated for their kill ratios. However, the larger silver particles were consistently only able to kill about 10% to 20% of the targeted pathogenic colonies of bacteria or viruses. Using a high resolution TEM (Transmission Electron-Microscope), a series of studies focused on both the ordinary nano-sized (0.02-0.20 microns or 20 nm to 200 nm (nanometers) as well as the mini-nano-sized (0.50 nm-10.0 nm (nanometers, which is the same as 0.00050-0.0010 microns) colloidal particles of pure silver. The sizes of the particles was confirmed with TEM analyses.

The main purposes of this project was to discover, test, develop, quantify and validate the practical applications of ultra-small silver particles (ranging in size from 0.4 nm to 2 nm (nanometers) in concentrations from 1 ppm-1,000 ppm as pathogenic eliminators utilizing electron-microscopy research to study the processes and effects of both the nano-sized and the much smaller mini-nano-sized colloidal particles of pure silver on extremely toxic and pathogenic bacteria.

During these years, a series of research phases was launched to investigate the biocidal annihilation of unwanted and pathogenic bacteria and viruses by colloidal silver. A brief history describing this important and related research is included herein because of its relevance to the unique Nine Key Restrictive Component Embodiments of the present invention. Even more than a decade ago, the smallness of the silver particles and their concentration number of single silver particles and ions was a key factor in the biocidal properties of the colloidal silver antimicrobial solutions.

The First Phase centered around the analyzing of the efficiency of attachment to pathogenic cells between the larger nano-sized (which often resulted in silver clumps) silver particles and the non-clumping (permanently stable) suspended mini-nano-sized colloidal particles of pure silver. The study of particle size clearly demonstrated that the smallest non-clumping mini-nano-sized colloidal particles of pure silver were far superior to the larger nano-sized molecules in remaining attached to the outside cell walls of the pathogenic bacterial and viral organisms.

Painstakingly created electron microscopy slides that quickly attempted to freeze the rapid annihilation of various lab cultured pathogenic organisms were analyzed in order to discover the sudden death processes of the nucleus and the implosion into protein trash fragments of targeted pathogenic cells when they were exposed to tiny silver particles (ranging from 0.4 to 2 nanometers in size) in a temperature controlled environment.

The Second Phase analyzed the biocidal penetration of various bacteria's cell membrane walls by comparing the biocidal activities of the larger nano-sized silver particles or compounds (ranging from 0.01 to 0.10 microns or 10 nm to 100 nm (nanometers in size). The larger particles usually contained numerous silver clumps that were unable to penetrate cell walls. Yet, in an identical environment, the very minute non-clumping (permanently stable) suspended mini-nano-sized (>2 nanometers) colloidal particles of pure silver exhibited the most efficient cell wall penetration. Thus, it became evident that the smallest silver particle size was extremely important for successful invasion of the bacteria cell wall and complete killing of the nuclei. Large particles and clumps of colloidal silver rarely penetrated even the thinnest or weakest sections of the bacteria cell wall. In rare cases where nano-sized particles or clumps of silver were able to stay attached to the cell wall but unable to invade it to reach the nucleus, the pathogen's cell wall did suffer some minor or major damage. In some cases, the minor damage to the cell by a large silver particle appeared to stimulate the replication process of the pathogenic organism. If the cell wall suffered only minor damage or if there was an insufficient number of lethal silver particles or compounds to annihilate the pathogenic organisms, the pathogens appeared to become stimulated.

The stimulation of pathogenic cells upon less than lethal contact to a biocidal agent is a process called hormesis, where a pathogenic organism has been exposed to a weak or ineffective biocidal agent but is not killed or severely damaged enough to not be able to replicate. When this occurs, the pathogen often replicates faster or becomes resistant to the antimicrobial agent.

The limited successes in annihilating pathogenic bacteria by the larger nano-sized particles and clumps of silver caused the researchers to discontinue the study of the larger silver colloidal particles in the next phases of the electron-microscopy research. Even though this hormesis was interesting to the university researchers, they chose to stay focused on the more exciting part of the studies, i.e., where tiny silver particles are able to exterminate an entire colony of pathogenic bacteria. As a sideline test, using the tiny silver particle solutions as a lab embalming agent, it was found that silver particles from 30 ppm to 60 ppm replaced a standard toxic "F" chemical.

The Third Phase of this special study investigated the genocidal behaviors of the minute mini-nano-sized colloidal particles of pure silver after they had managed to get inside the cell organism. Several key factors (One) ultra-smallness of size and (Two) concentration (ranging between 1 ppm-6 ppm) resulted in the highest kill ratios and desirable death curves (kill percentages>90% on contact or in less than 5 minutes). Of particular interest was the consistent attachment to the core nucleus of the bacteria cell by the positively charged mini-nano-sized colloidal silver particles.

This part of the electron microscopy research was frequently frustrating to the team of university researchers that had joined the inventor and Dr. Goodman due to the unusual behaviors of the silver particles that were witnessed by the team when the tiny colloidal silver particles were exposed to a colony of pathogens. This type of research was very difficult because of the rapid extermination of the pathogens when exposed to pure silver particles.

Generally, the whole colony (with all its pathogenic cells being killed) was exterminated on contact or within a few minutes of being exposed to the tiny silver particles suspended in a pure aqueous distilled water medium. The annihilation of the entire colony happened so fast that it was difficult and often impossible to capture the stages of the genocide process in order to prepare slides for the electron microscope.

The Fourth Phase of the research centered on the phenomenal implosion and ruination of the diseased or pathogenic cells into small protein fragments soon after the positive mini-nano-sized colloidal silver particle became bonded with the negatively charged nucleus. This complete and instant destructive fragmentation of the nucleus and the entire pathogenic cell into harmless protein particles was observed repeatedly soon after the mini-nano-sized colloidal particles of pure silver attached to the nucleus.

This disintegration mechanism appeared similar in process to the lethal actions and processes of the larger Immunocompetent white blood cells known as "NK cells" that have been observed invading and imploding targeted pathogenic organisms in the vicinity of the lymphocytic "NK cell." In both cases, the targeted pathogenic cell is invaded and left in small non-toxic fragments of trash to be disposed of by normal excretion processes.

The Fifth Phase of this colloidal silver research project was focused on the rapid extermination of the nucleus of a pathogenic cell. A UCSF volunteer team of seasoned microbiologists (who helped with the experimental studies) found it quite difficult to capture the stages of the fast genocide process between the suspended silver particles and the targeted cells. The reason for this was due to the rapid invasion of the cell wall by the silver particle and the almost immediate (within seconds) destruction of the entire cell organism after the silver had electrically bonded with the core nucleus. Many unsuccessful attempts were made to "freeze frame" the few milliseconds of events after the silver was once ingested inside the cell wall. Without visual proof, the UCSF researchers concluded that the strong positively charged silver particle somehow electrocuted the negatively charged nucleus of the pathogenic cell. But, the process happens so rapidly, it is very difficult (or impossible) to actually capture on electron microscopy slides what had happened inside the cell wall. This research was likely the beginning of the silver nanotechnology industry. Many hundreds of hours where spent on numerous experiments that were conducted by seasoned microbiologists, lab techs and microscopists hoping to find a way to capture, describe and quantify the short sequences of how the positively charged silver particle invaded the cell wall and then quickly moved towards the center nucleus and destroyed it. Was it cellular electrocution? Or, were the Ag molecules so poisonous to the nucleus that it self-destructed into protein fragments?

An unprecedented opportunity showed up for the researchers at an eight story building in Washington State's capital that had a toxic killer mold growing in the crawl space between the first floor and the ground. The building was condemned and the occupants forced to move out. The owner was distraught, because the only known remedy for such a toxic condition was burning the building to the ground and rebuilding it. Of course, there was no insurance for such an option. The researchers proposed an experiment with a custom formula of tiny silver particles as a genocide agent to safely eradicate the black mold that made the building unsafe and unusable for humans. The owner offered to pay for the test and if successful in killing the mold, he would contribute to the university research project for saving his commercial property. Not only was the test successful under the first floor, but toxic mold spores throughout the building were eliminated by "custom formulas" of the minute silver particles.

Until microscope technology catches up with the needs of this nanotechnology industry, these research questions will likely remain unanswered until microscopes can capture a computerized film for a short movie that reveals the microscopic life bioactivities of a mini-second long life process where the microscope magnification needed to watch such an event requires at least 150,000 to 200,000 magnifications. In the mean-time, nanotechnologists and microbiologists are continuing to study mostly commercially viable smaller and smaller colloidal silver compounds and particles prepared by producing silver nanoparticles, ions or a variety of silver compounds through facile synthesis, impregnating biological plants, chemical compounding, biochemical or other biological processes. Others are creating or preparing silver nanoparticles, ions or compounds through the use of aqueous solutions of plant extracts as bioreductants. Most of these laboratory and/or commercially viable processes are focused on economically supported research that results in profitable products that can yield significant ROI to the funders of the research.

The above controlled lab experiments included many pathogenic organisms, such as:

Gram Positive Bacteria—Including: *Actinobacteria, Actinomyces, Actinomyces georgiae, Actinomyces gerencseriae, Actinomyces israelii, Bacillales, Bacillus, Bacillus* mojavensis, Bacillus weihenstephanensis, Clostridium, Clostridium acetobutylicum, Clostridium aerotolerans, Clostridium argentinense, Clostridium autoethanogenum, Clostridium baratii, Clostridium beijerinckii, Clostridium bifermentans, Clostridium botulinum, Clostridium butyricum, Clostridium cadaveris, Clostridium cellobioparum, Clostridium cellulolyticum, Clostridium cellulovorans, Clostridium chauvoei, Clostridium clostridioforme, Clostridium colicanis, Clostridium difficile, Clostridium estertheticum, Clostridium fallax, Clostridium formicaceticum, Clostridium histolyticum, Clostridium innocuum, Clostridium kluyveri, Clostridium ljungdahlii, Clostridium novyi, Clostridium paradoxum, Clostridium paraputrificum, Clostridium clostridioforme, Clostridium colicanis, Clostridium difficile, Clostridium estertheticum, Clostridium fallax, Clostridium formicaceticum, Clostridium histolyticum, Clostridium innocuum, Clostridium kluyveri, Clostridium ljungdahlii, Clostridium novyi, Clostridium paradoxum, Clostridium paraputrificum, Clostridium perfringens, Clostridium phytofermentans, Clostridium piliforme, Clostridium ragsdalei, Clostridium ramosum, Clostridium saccharobutylicum, Clostridium saccharoperbutylacetonicum, Clostridium scatologenes, Clostridium septicum, Clostridium sordellii, Clostridium sporogenes, Clostridium stercorarium, Clostridium sticklandii, Clostridium straminisolvens, Clostridium tertium, Clostridium tetani, Clostridium thermosaccharolyticum, Clostridium tyrobutyricum, Clostridium uliginosum, Corynebacterium, Corynebacterium amycolatum, Corynebacterium bovis, Corynebacterium diphtheriae, Corynebacterium efficiens, Corynebacterium granulosum, Corynebacterium jeikeium, Corynebacterium macginleyi, Corynebacterium minutissimum, Corynebacterium renale, Desulfitobacterium dehalogenans, Enterococcus, Fervidobacterium changbaicum, Fervidobacterium gondwanense, Fervidobacterium islandicum, Georgenia ruanii, Lactobacillales, Listeria, Listeriaceae, Microbispora corallina, Nocardia, Nocardia asteroides, Nocardia brasiliensis, Nocardia farcinica, Nocardia ignorata, Pasteuria, Propionibacterium acnes, Rhodococcus equi, Sarcina (genus), Solobacterium moorei, Sporosarcina, Sporosarcina aquimarina, Sporulation in Bacillus subtilis, Staphylococcus, Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus muscae, Staphylococcus nepalensis, Staphylococcus pettenkoferi, Staphylococcus pseudintermedius, Staphylococcus saprophyticus, Staphylococcus schleiferi, Staphylococcus succinus, Staphylococcus warneri, Staphylococcus xylosus, Strangles, Streptococcus, Streptococcus agalactiae, Streptococcus anginosus, Streptococcus bovis, Streptococcus canis, Streptococcus downei, Streptococcus faecalis, Streptococcus gordonii, Streptococcus iniae, Streptococcus lactarius, Streptococcus mitis, Streptococcus mutans, Streptococcus oralis, Streptococcus parasanguinis, Streptococcus peroris, Streptococcus pneumoniae, Streptococcus pyogenes, Streptococcus ratti, Streptococcus salivarius, Streptococcus sanguinis, Streptococcus sobrinus, Streptococcus suis, Streptococcus thermophilus, Streptococcus tigurinus, Streptococcus uberis, Streptococcus vestibularis, Syntrophomonas curvata, Syntrophomonas palmitatica, Syntrophomonas sapovorans, Syntrophomonas wolfei, Syntrophomonas zehnderi, and Viridans streptococci.

Gram Negative Bacteria—Including: Acetic acid bacteria, Acinetobacter baumannii, Agrobacterium tumefaciens, Anaerobiospirillum, Anaerolinea thermolimosa, Anaerolinea thermophila, Arcobacter, Arcobacter skirrowii, Armatimonas rosea, Bacteroides, Bacteroides fragilis, Bacteroides ruber, Bartonella japonica, Bartonella koehlerae, Bartonella taylorii, Bdellovibrio, Brachyspira, Caldilinea aerophila, Cardiobacterium hominis, Chaperone-Usher fimbriae, Chthonomonas calidirosea, Coxiella burnetii, Cyanobacteria, Cytophaga, Dialister, Enterobacter, Enterobacter cloacae, Enterobacter cowanii, Enterobacteriaceae, Enterobacteriales, Escherichia, Escherichia coli, Escherichia fergusonii, Fimbriimonas ginsengisoli, Fusobacterium necrophorum, Fusobacterium nucleatum, Fusobacterium polymorphum, Haemophilus felis, Haemophilus haemolyticus, Haemophilus influenzae, Haemophilus pittmaniae, Helicobacter, Helicobacter pylori, Klebsiella pneumoniae and oxytoca, Kluyvera ascorbata, Kluyvera cryocrescens, Kozakia baliensis, Legionella, Legionella pneumophila, Leptotrichia buccalis, Levilinea saccharolytica, List of strains of Escherichia coli, Luteimonas aestuarii, Luteimonas aquatica, Luteimonas composti, Luteimonas lutimaris, Luteimonas marina, Luteimonas mephitis, Luteimonas vadosa, Megamonas, Megasphaera, Meiothermus, Methylobacterium fujisawaense, Morax-Axenfeld diplobacilli, Moraxella, Moraxella bovis, Moraxella osloensis, Morganella morganii, Negativicutes, Neisseria cinerea, Neisseria gonorrhoeae, Neisseria meningitidis, Neisseria sicca, Nitrosomonas eutropha, Nitrosomonas halophila, Nitrosomonas oligotropha, OMPdb, Pectinatus, Pelosinus, Pontiac fever, Propionispora, Proteobacteria, Proteus mirabilis, Proteus penneri, Pseudomonas, Pseudomonas aerugio/nosa, Pseudomonas genome database, Pseudomonas luteola, Pseudoxanthomonas broegbernensis, Pseudoxanthomonas japonensis, Rickettsia rickettsii, Salmonella, Salmonella bongori, Salmonella enterica, Salmonella enterica subsp. enterica, Samsonia, Selenomonadales, Serratia marcescens, Shigella, Sorangium cellulosum, Sphaerotilus, Spirochaeta, Spirochaetaceae, Sporomusa, Stenotrophomonas, Stenotrophomonas nitritireducens, Thermotoga neapolitana, Trimeric autotransporter adhesin, Vampirococcus, Verminephrobacter, Vibrio adaptatus, Vibrio azasii, Vibrio campbellii, Vibrio cholerae, Vitreoscilla, Wolbachia, YadA bacterial adhesin protein domain, and Zymophilus.

Gram Indeterminant Bacteria—Including: Amphitrichous, Anthrax Bacilli, Atrichous, Borellia, Cervical Lymphadenitis, Chlamydiae, Chloroflexi, Chrysiogenetes, Deinococcus-Thermus, Dictyoglomi, Diphtheria, Drug Multi-Resistant-Tuberculosis/Cellulitis, Elusimicrobia, Endospores, Fibrobacteres, Firmicutes, Gemmatimonadetes, Hepatitus B, Heterotrophic, Lentisphaerae, Lupus Vulgaris, Osmophiles, Nitrospira, Nocardia Asteroides, Papulonecrotic Tuberculid, Pericarditis, Planctomycetes, Synergistetes, Tenericutes, Tetanus, Treponema, and Tuberculoid and Histoid Leprosy, Urogenital Tuberculosis, and Verrucomicrobia.

Viruses—Including: Cryptococcus gattii, Enterovirus, Orthomyxoviridae, Piconavirus, Coronavirus, Rhinovirus, and Rotovirus, norovirus.

Molds—Including: Alternaria, Aspergillus, Cladosporium, Penicillium, Stachybotrys chartarum, and Trichoderma harzianum.

Fungi—Including: Candida albicans, Candida parasilosis, Histoplasma capsulatum, Crytococcus neoformans, Coccidioides (valley fever), Dermatophyte (Atheletes foot), Exserohilum rostratum,

DESCRIPTION AND ANALYSES OF PRIOR ART

There are no exact uses or previous applications envisioned that might be possible, even with drastic modifications, in any of the prior art described or analyzed herein. Thus, none of the prior art relates in any manner whatsoever to the unique intended uses and applications of this invention.

U.S. Pat. No. 6,027,469 is directed to a limited disinfectant application with specific uses for disinfecting dialysis equipment only, Lee Johnson, listed as the inventor. Even though this application utilizes ionized particles of silver, they tend to clump, will not mix, and otherwise "fall out of suspension," because the patent teaches the producing of them using high-voltage (440 volts) silver generators which produce particles and compounds much too large (5 to 15 nanometers) to kill the intended pathogens in the dialysis equipment. Thus the silver particles are: (A) not manufactured small enough; (B) manufactured in too high of concentrations, or when they come in proximity with any other "Anti" charge elements including any metal, they tend to bond and form an inert compound with no biocidal or antimicrobial properties. Initially, over 95% of the research, know-how, drafting of the patent application specs as well as the technical expertise supporting the applicational method was done by Joseph R. Goodman, Ph.D., and Paul Ash Minturn, Ph.D., (Lee's close friends). They designed and supervised the entire extensive laboratory and electron microscopy lab validation studies that were conducted at the Pediatrics Electron Microscopy Research Dept. of the University of California at San Francisco. Though promised, but not named as the co-inventors, the world owes them a big thank you for self-lessly contributing to this important innovative "green" solution that is a nightmare for both the EPA and FDA in dealing with very toxic chemicals that harm or kill thousands of people each year involved in the ever growing Hemo-Dialysis Industry. At the very last minute, the patent attorney and Lee Johnson (not consulting with his close friends) made some last minute changes in the Application by changing its low-voltage manufacturing process (less than 24 volts) to a high-voltage (440 volts) mistakenly thinking it would make it possible to produce faster and greater quantities of the silver colloidal solutions. This did not change its patentability, but it did weaken the disinfecting abilities of the silver colloidal solutions. The silver particles produced ended up larger than five nanometers with a yellowish oxide coating, lowering their ultimate effectiveness at exterminating the unwanted organisms that must be eliminated inside the chambers of the Hemo-Dialysis Equipment before it can be used by other patients.

The Silver Edge, a marketing firm in Arizona, promotes silver nanotechnology though informative articles and publications in non-technical laymen's languages, also sells a colloidal silver generator that produces tiny silver particles at 0.0008 microns (i.e., 0.8 nanometers). The art suggests large, unknown concentrations of sliver particles and ions that range in numbers from a few thousand to 5 million particles, but this art cannot qualify for the stringent requirements set forth in the nine key restrictive component embodiments. See informational and educational articles at: The Silver Edge http://www.thesilveredge.com/ or, httplithesilveredge.com/ppm.shtml#.VB4Vp-ktCM8.

Need for Safe "Green" Biocidal Solutions that Annihilate Pathogens

Desperate Need for Safe "Green" Biocidal Solutions for a Healthier Sustainable World The Problem: —Wide Spread Use of Dangerous Toxic Chemical Products Every year thousands (millions world-wide) are injured, disabled or killed by repetitive exposure to embalming, sterilizing, disinfectant, preservative, mold and fungi eradication agents that can be even life threatening due to cumulative effects from toxic substances, such as: Chlorox, iodine, hydrogen peroxide, formaldehyde, alcohol, etc.

Handling the waste products from these toxic substances costs many millions (billions world-wide) of dollars while threatening future youth generations and the ecological balances of nature on Mother Earth.

Many "green" products are helpless against the increasing pandemic uncontrolled growth and rapid genetic variations of bacteria, viruses, molds and fungi that have been treated with toxic substances that kill both "good" (probiotics needed for optimal health and ecological balance) and "bad" (pathogenic) micro-organisms.

The Solution: —Replace With Safe Non-Toxic "Green" Solutions That Kill Pathogens The present invention teaches safe "green-type" non-toxic custom formulated solutions that effectively kill only the unwanted pathogenic micro-organisms while helping the "good" probiotic ones keep ecological balances in targeted environments. There are lucrative worldwide industries and market places waiting for these solutions, including: disinfectants for travel (airplanes, airports, trains, buses, hotels, cruise ships, etc.); the industry size is over $7 trillion; sterilization (hospitals, clinics, medical, dental, and veterinary offices, medical labs, blood banks, etc.); the industry size is over $900 billion; embalming (mortuaries, funeral homes, forensic labs, etc.); the industry size is over $8 billion; mold and fungi eradications (in commercial, industrial and residential settings); the industry size=huge; and, food/drink prevention of decay, the industry size=astronomical.

The present invention teaches safe formulated "green-type" non-toxic biocidal antimicrobial methods for producing pure mini-nano-sized colloidal silver particle and ion solutions that effectively eradicate unwanted and/or pathogenic organisms by killing over 90% of targeted pathogens. These pure elemental mini-nano-sized silver solutions can efficiently replace the toxic chemicals commonly used in the industry environmental settings above. Most "green" products aimed at these world-wide problems have very low effective kill ratios and/or death curves (usually 25% or less) and are inept at solving the constantly escalating environmental problems of pathogens. The present invention is the only known "green" answer that can replace the toxic agents currently polluting the environment and harming or killing many people. Thus there exists an ever growing world-wide need for proven safe "green" solutions that match the 90+% kill ratios of the toxic chemicals and other substances addressing these big concerns.

SUMMARY OF THE INVENTION

Creating the Perfect Silver Bullets to Annihilate Unwanted/Pathogenic Organisms

As the number, toxicity levels and potential pandemic conditions of multiple resistant strains of mutant bacteria, viruses, molds and fungi increases in the world's ecosystem, there exists a critical search and need for safe, "green-type," non-toxic customized highly efficient biocidal agents (which means that the agent or solution has very high kill ratios>90% and ideal death curves of <5 minutes up to 24 hrs) that do not create environmental hazards, or drug resistant mutations in the biological organisms targeted for annihilation, stimulation of the pathogenic organisms and/or any negative reactions or changes to the biocidal exterminator itself.

The solution to this escalating problem can be found in safe, "green-type," non-toxic biocidal solutions composed of custom combinations of "ideal sizes and concentrations" (i.e., the tested combinations that yield the highest kill ratios and death curves as determined by both lab and field tests) of bioavailable (meaning unattached, not clumped or bonded to any other element or ion) mini-nano-sized (sizes between 0.04 mini-nanometers [mnm] and 0.99 mnm) single individual silver particles and ions composed only of ultra-tiny pure individual silver particles and ions in suspension.

The most important key factors to consider are smallness of size, ideal concentration as well as their bioavailability. These attributes of the single individual silver particles and ions may be the most important considerations in finding the most efficient and effective biocidal mini-nano silver solutions. There are many studies that confirm the fact that larger sizes, such as 11 nanometers to 1,000 nanometers of the silver particles, ions and silver compounds often cause unwanted side effects or discolorations and generally are only minimally effective in killing, destroying, eradicating or retarding the growth of unwanted biological or chemical changes and/or pathogenic organisms.

The present invention provides the perfect answer to this world-wide search with safe, "green-type," non-toxic exterminator formulas that eradicate but do not create multiple resistant strains of mutant bacteria, viruses, molds and fungi in the targeted unwanted and/or pathogenic organisms or cause unwanted toxic environmental conditions. This invention combines the data from tightly controlled laboratory experimentations as well as specially administered field test studies conducted in order to determine the optimal combination of particle and ion sizes of the pure single stand-alone silver particles and ions, plus their ideal concentration (the number of single bioavailable nanosilver particles and ions per liter, i.e., nsbnsip/l) that effectively and efficiently function as safe, non-toxic "green-type" biocidal agents.

Glossary and Definition of Terms in Application

NOTE: A special glossary and definition of terms used in this application is included herewith in order to fully explain the unique and specialized meanings of both new as well as some terms with different meanings for this application and invention that are used differently from their common general usage in the nanotechnology industry. The specialized uses and meanings of these terms are incorporated as an integral part of the "Specifications" for this technology and art. For any person with ordinary skills in the art, the present invention uses special specific terms and language as defined in the glossary and set forth here in the preferred embodiments and claims. It nevertheless should be understood, by anyone with experience and expertise in the art, that no limitation of the scope of the invention is hereby intended.

Specialized New Terms and Meanings Used in Patent Application

Argyria—refers to a rare discoloring or graying of the skin when a person is exposed to excessive amounts of silver Application—refers to a series of simple steps, procedures and/or protocols that can be used by a person with ordinary skills in the art to implement the nine restrictive preferred embodiments of this invention in preparing and producing a biocidal substance solution containing pure mini-sized silver particles and ions in suspension in an aqueous water solution Bacterial Actions—refers to the rapid and exponential growth of bacteria Bacterial-Destroying, Prophylactic Biocidal Substance Medical Device—means a substance or solution that retards, eliminates, destroys, exterminates, annihilates or kills unwanted bacterial pathogenic organisms "BAD" Organisms—refers to unwanted and/or deadly, dangerous disease causing or pathogenic organisms Best Death Curve Possible (BDCP)—refers to a consistently high biocidal death curve where in greater than 90% annihilation of any targeted micro-organism occurs on contact or in less than 5 minutes Bioavailable—refers to the biological availability of a substance, particle or organism that is not attached, bonded or controlled by any other agent, organism or substance in an ecological balanced environment. Example: A bioavailable silver particle is a single individual mini-nanosized silver particle that is not bonded, ionized, combined or attached to any other element Biocidal—means the same as anti-microbial substance or solution that has the ability, attributes and actions for retarding growth or eliminating/annihilating unwanted biological organisms and micro-organisms Biocidal Application—means an application that has the same abilities, attributes and actions as an anti-microbial application which has the ability to retard growth or eliminate/annihilate unwanted biological organisms and micro-organisms Biocidal Mini-Nano-Silver Solutions—refers to biocidal mini-nano-silver solutions that have anti-microbial attributes and capabilities Biocidal Solutions—means custom formulated antimicrobial genocidal solutions, agents, substances or compounds that annihilate unwanted and/or pathogenic growths and/or organisms Clarity or Clearness of Silver Solutions—refers to the clearness and absence of turbidity of the aqueous solution with the (mnm) mini-nanometer sized silver particles in a colloidal suspension Colloidal Silver Mini-Particle Solutions—means a custom formulated solution according to the nine key restrictive preferred embodiments of the "Specifications" containing ultra-pure water and the preferred number according to the method of mini-nanometer sized silver particles in a colloidal suspension. The pure silver solution contains silver particles and ions. It is considered a pure colloid. The particles remain suspended in the water indefinitely owing to a silver particle charge which causes an electrostatic mutual repulsion of other silver particles.

Colloidal Silver Mini-Particle Stability—refers to the stability is determined by any interaction between individual silver particles in solution. Long term stability exists when mutual repulsion exists between particles in a colloid causing the dispersant to resist flocculation or coagulation Concentration—The total number of estimated, calculated or measured mini-silver nano-particle parts per million of suspended single individual silver particles (or materials, i.e., solute) in an aqueous water solution.

Commonly Correlated PPM—This refers to the commonly correlated usage of the ppm (parts per million) terms that refer to the total weight (and not the actual number of particles or ions) of the pure silver particles, ions and any silver compounds suspended in a solution or clumped at the bottom of the container. This common correlated use of the ppm is not an actual estimated counting of the single individual silver particles or ions in suspension in the solution Conventional PPM—refers only to the wide spread usage of the ppm (parts per million) terms as referring to the total weight of the pure silver particles, ions and any silver compounds suspended in a solution or clumped at the bottom of the container Crystal Clear Silver-Particles and Ions (CCSPI)—refers to the crystal clearness of a colloidal silver particle and ion solution Crystal Clearness—refers to totally clear solutions of colloidal silver particles and ions Customized Application—refers to a special application using the nine preferred embodiments of the present invention that can be utilized by a person with ordinary skills in the art to implement the nine restrictive preferred embodiments of this invention in preparing and producing a biocidal substance solution containing pure mini-sized silver particles and ions in suspension in an aqueous water solution Customized Applications of the specific formulated biocidal substance solution—refers to special customized applications of the specific formulated biocidal substance solutions utilizing the nine preferred embodiments of the present invention Customized Biocidal Applicational Method—relates a customized method for implementing the nine preferred embodiments of the present invention, which are used therein to refer to an applicational method of creating, preparing and producing special formulated antimicrobial genocidal customized solutions according to the specifications of this invention Customized Biocidal Agents—These are special terms that relate to the implementation of the nine preferred embodiments of the present invention referring to creating, preparing and producing special formulated antimicrobial genocidal customized solutions or agents Custom Combination of Ideal Size and Concentration—refers to the combing of the ideal size of silver particles and ions as determined by the suggested evaluational tests and comparative experiments according to the nine preferred embodiments and then combining the ideal size with the ideal concentration of silver particles and ions as determined by the suggested evaluational tests and comparative experiments according to the nine preferred embodiments Customized Design Procedures—refers to the detailed steps utilizing the nine preferred embodiments of the invention to design procedures for preparing and producing special customized biocidal antimicrobial solutions Customized Formulas—refers to creating a customized formulas for preparing and producing special customized biocidal antimicrobial solutions Customized Precise Formulations—refers to creating precise customized formulas for preparing and producing special customized biocidal antimicrobial solutions Customized Protocols for identifying, evaluating, testing, preparing, producing and manufacturing aqueous biocidal silver formulas—refers to the simple steps and protocols that can be utilized by one with ordinary skills in the art wishing to prepare and produce biocidal antimicrobial solutions according to the embodiment of this invention Customized Liquid Solution—refers to creating customized liquid solutions according to the formulas of this invention for preparing and producing special customized biocidal antimicrobial solutions Customized Specialized Formulations—refers to preparing of custom formulated solutions according to the five embodiments of the "Specifications" containing pure water and the specified preferred number of mini-nanometer sized silver particles in a colloidal suspension Dangerous Infectious Condition—refers to a setting where serious and/or dangerous toxic and/or infectious conditions exist in an environmental ecosystem Death Curve—A death curve is herein defined as the relative amount of time it takes to achieve a desired specific high Kill Ratio greater than 90% in less than 5 minutes. Example: For effective biocidal genocide of unwanted or pathogenic organisms, a Death Curve of less than 5 minutes is desirable.

Environmental Improvement Agent—refers to either a substance or solution that helps to improve the ecological balances of an environmental ecosystem Environmental Biological Change—refers to a significant biological change in an organism when exposed to a specific formulated biocidal substance solution Environmental Chemical Change—refers to a significant chemical change in the environmental ecosystem in which organism lives when exposed to a specific formulated biocidal substance solution Environmental Setting—refers to the targeted environmental ecosystem in which the biocidal substance solutions are being applied and implemented according to the nine restrictive embodiments of this invention whether in a laboratory or actual field setting Exterminating Medical Device—as used in the embodiments and claims of the present invention, an exterminating medical device consists of a special formulated biocidal antimicrobial solution that is capable of reducing, eliminating, annihilating or killing unwanted and/or pathogenic organisms Fungal Biocidal Solution—refers to a substance or solution that retards, eliminates, destroys, exterminates, annihilates or kills unwanted fungal pathogenic organisms Fungal-Destroying, Prophylactic Biocidal Substance Medical Device—means a substance or solution that retards, eliminates, destroys, exterminates, annihilates or kills unwanted fungal pathogenic organisms Fungal Growths—refers to an explosive growth of fungi in an environmental ecosystem Germ-Destroying Prophylactic Biocidal Substance Medical Device—refers to a specific formulated biocidal substance solution that can be utilized as a prophylactic germ-destroying agent GOOD Organisms—Refers to vital health enhancing needed organisms for balanced ecologically healthy environments. Example: There are a number of vital probiotic friendly organisms (such as: *acidophilus, lactobacillus*, enzymes, flora and fauna and other "GOOD" organisms) that play important roles in maintaining the healthy functioning of human, animal and plant organisms Gram Indeterminant Bacterial Biocidal Solution—refers to a substance or solution that retards, eliminates, destroys, exterminates, annihilates or kills unwanted gram indeterminant bacterial pathogenic organisms Gram Indeterminant Bacterial-Destroying, Prophylactic Biocidal Substance Medical Device—means a substance or solution that retards, eliminates, destroys, exterminates, annihilates or kills unwanted gram indeterminant bacterial pathogenic organisms Gram Indeterminant Bacterial Growths—refers to an explosive growth of gram indeterminant bacteria in an environmental ecosystem Gram Negative Bacterial Biocidal Solution—refers to a substance or solution that retards, eliminates, destroys, exterminates, annihilates or kills unwanted gram negative bacterial pathogenic organisms Gram Negative Bacterial-Destroying, Prophylactic Biocidal Substance Medical Device—is a substance or solution that retards, eliminates, destroys, exterminates, annihilates or kills unwanted gram negative bacterial pathogenic organisms Gram Negative Bacterial Growths—refers to an explosive growth of gram negative bacteria in an environmental ecosystem Gram Positive Bacterial Biocidal Solution—refers to a substance or solution that retards, eliminates, destroys, exterminates, annihilates or kills unwanted gram positive bacterial pathogenic organisms Gram Positive Bacterial-Destroying, Prophylactic Biocidal Substance Medical Device—means a substance or solution that retards, eliminates, destroys, exterminates, annihilates or kills unwanted gram positive bacterial pathogenic organisms Gram Positive Bacterial Growths—refers to an explosive growth of gram positive bacteria in an environmental ecosystem Green Type—Refers to the commonly accepted concept of anything (humans, animals, plants or elements) that is safe, non-toxic and contributes positively to a sustainable future for Mother Earth and all non-pathogenic or parasitic living organisms.

Green-type non-toxic exterminator formula—means a safe biocidal formulated solution as set forth herein.

High Voltage-High Voltage is hereby defined as any voltage greater than 26 Volts, DC or AC, for all manufacturing equipment creating, making or producing nanosized silver particles, ions or compounds as defined herein. It should be noted here that High Voltage colloidal silver manufacturing equipment generally produce and/or create relatively large nanosized silver particles, ions or compounds (usually larger than 200 nm), but are incapable of creating, making or producing any of the ultra-small mini-nanosized silver particles or ions as defined herein.

Healthful, safe, sustainable biologically balanced ecological environment—refers to an environmental ecosystem that is healthful, safe and sustainable for biological organisms, whether human, animal or plant Homeopathic Dosage—refers to a very small dosage amount of an active ingredient, substance or solution that causes no harm even if the desired result does not happen Homeopathic Medicine—refers to a healing art and science in which a very small dosage amount of an active ingredient, substance or solution is administered that can cause no harm even if the desired result does not happen Highest Kill Ratio Possible (HKRP)—for this invention, the highest kill ratio possible refers to the outcomes of tests done to determine which size and concentration of the mini-nanosized silver particles and ions yield the best kill ratio when the biocidal solutions of colloidal silver are exposed to selected pathogenic organisms Ideal Limited Number of Silver Particles/Ions—refers to an estimated number count of the pure silver particles and ions in suspension that produce the most ideal outcomes Total Ideal Number (TIN)—refers to an estimated number count of the pure silver particles and ions in suspension that produce the most ideal outcomes Ideal Concentration—The "ideal concentration" is defined as the ideal tested number of single bioavailable mini-nanosilver particles per liter that effectively and efficiently function as a non-toxic safe "green-type" biocidal agent that consistently produces the highest kill ratio and death curve on targeted unwanted and/or pathogenic organisms. Since there can be too much of a "GOOD" thing (including too many silver particles and ions), the "ideal concentration" is an adjusted and tested number of silver particles and ions that repeatedly produces the best results in kill ratios and death curves. The "ideal concentration" is also desirable because it does not cause any harm to the ecosystem environment; nor does it cause any toxic wastes.

Ideal Biocidal Solution—Refers to a consistently high kill ratios and timed death curves for anti-microbial customized specially formulated solutions.

Ideal Death Curve (IDC)—refers to a consistently high biocidal timed death curve where in greater than 90% annihilation of a targeted micro-organism occurs on contact or in less than 5 minutes Ideal Size—For this invention, the ideal size refers to the measured mini-nanometer diameter of pure silver particles and ions in indefinite suspension in pure water.

Ideal Solution—In an ideal solution, the molecules in the solution do not interact with each other and the concentration and the activity are identical.

Ideal pure biocidal single individual bioavailable large-nano-silver particles—refers to sizes of 10 nm to 1,000 nm (nanometers)

Ideal small pure biocidal single individual bioavailable nanometer silver particles—ideal "small" refers to sizes between 1.0 nm and 9.9 nm (nanometer)

Ideal tiny pure biocidal single individual bioavailable mini-nano-silver particles (itpbsibmnsp) ideal "tiny" refers to tiny silver particle and ion sizes between 0.04 mnm and 0.99 mnm (mini-nanometers).

Immunocompetency Functioning—refers to the balanced, efficient and highly competent functioning of the immune system in the presence of pathogens Kill Ratio—Refers to the measured percentage of targeted organisms that are killed or annihilated by a biocidal agent. Example: For effective biocidal genocide of unwanted or pathogenic organisms, a high Kill Ratio greater than 90% is desirable.

Liquefied Stable Suspended Preparation—refers to an attribute of the special formulated biocidal antimicrobial solution that is indefinitely stable in suspension in an aqueous water solution Low Voltage—for this invention, low-voltage means a DC voltage that is less than 26 Volts, for all manufacturing equipment creating, making or producing either nanosized silver particles or ions or mini-nanosized silver particles or ions as defined herein. It should be noted here that only Low Voltage Colloidal Silver Generators have the ability to create, make or produce any of the ultra-small mini-nano-sized silver particles or ions as set forth herein.

Low Voltage Produced Silver Particles and Ions—refers to tiny mini-nanometer sized silver particles and ions produced by a low DC voltage (<26 v)

Maximum Purity—refers to the highest level of purity for the super-distilled water that is used as the medium for suspension of the silver colloids for the biocidal solutions Microbial Action—refers to actions, reactions and any unwanted effects caused by microbial organisms especially rapid population growth and replications of pathogenic disease-causing micro-organisms Mini-Nano-Meters—refers to diameters between 0.04 nm and 0.99 nm (nanometers) which is the same as 0.00004 microns and 0.00099 microns Mini-nanosized Bioavailable Silver Particles—Refers to bioavailable silver particles ranging in size from 0.04 mnm to 0.99 mnm (mini-nanometers) in diameter Minute Mini-Nano-Sized Silver Particles—Refers to bioavailable silver particles ranging in size from 0.04 mnm to 0.99 mnm (mini-nanometers) in diameter Mold Biocidal Solution—refers to a substance or solution that retards, eliminates, destroys, exterminates, annihilates or kills unwanted mold pathogenic organisms Mold-Destroying, Prophylactic Biocidal Substance Medical Device—means a substance or solution that retards, eliminates, destroys, exterminates, annihilates or kills unwanted pathogenic mold organisms Mold Growths—refers to an explosive growth of molds in an environmental ecosystem Natural Medicine—refers to substances that have not lost their natural attributes via commercial processing that have been produced by nature and which may be used as medicines without causing any harm Non-Clumping Biocidal Substance Solution—refers to the single bioavailable clear biocidal substance solutions composed of mini-nanosilver particles that stay in suspension indefinitely and do not clump or form larger molecules and/or settle to the bottom of a container Non-Clumping Mini-Nanosized Silver Particles—refers to the single bioavailable clear mini-nanosilver particles that stay in suspension indefinitely and do not clump or form larger molecules and/or settle to the bottom of a container Non-Toxic—refers to a safe and sustainable attribute of anything (substance or element) that causes no short or long-term harm, and does not create any substance resistant mutations in any targeted unwanted and/or pathogenic organisms Non-Toxic Liquid Specific Formulated Biocidal Substance Solutions—refers to the safe and sustainable attributes of the pure silver non-toxic liquid specific formulated biocidal substance solutions prepared and produced according to the nine restrictive embodiments of the present invention Number of single bioavailable nanosilver particles/ions per liter—refers to the estimated count of the number of individual unattached colloidal silver particles and ions in suspension in a liter of pure distilled aqueous water solution Optimal Combination of Particle/Ion Size—refers to the combing of the ideal size of silver particles and ions as determined by the suggested evaluational tests and comparative experiments according to the nine preferred embodiments and then combining the ideal size with the ideal concentration of silver particles and ions as determined by the suggested evaluational tests and comparative experiments according to the nine preferred embodiments Pure Silver—meaning an Ag fineness of 0.9999+ purity Quality Control—refers to a process of evaluating a produced biocidal substance solution assuring that it meets or exceeds certain predetermined specifications Resistant Strains of Mutated Organisms—refers to any microbial pathogenic organism that develops and replicates into mutant strains that are multi-drug and methylcillin resistant organisms (such as: strains of bacteria, viruses, mold and fungi)

Stable Suspension—refers to the length of time that the mini-nanosized bioavailable silver particles and ions maintain their indefinite suspension and biocidal attributes in a pure distilled aqueous water solution Safe, Non-Toxic, Green Type Potent Eco-Friendly Biocidal Agent—refers to the safe and sustainable attributes of the pure "green" silver non-toxic liquid specific formulated biocidal substance solutions prepared and produced according to the nine restrictive embodiments of the present invention Selective Genocide Biocidal Substance—refers to the attributes and capabilities of the specific biocidal formulated solutions which are lethal only to unwanted and/or pathogenic organisms and cause no harm to friendly probiotic organisms Quality Control—Means a process of evaluating a produced product assuring that it meets or exceeds certain predetermined specifications.

Resistant strain of mutant organism (bacteria, virus, mold, fungi)—refer to strains of Gram Positive Bacteria, Gram Negative Bacteria, Gram Indeterminant Bacteria, Viruses, Molds and Fungi that have developed multiple drug resistances Selective Biocidal Genocide—This expression describes the biocidal attributes of certain genocidal agents that only annihilate specific unwanted and/or pathogenic ("BAD") organisms but has no negative affect on other ("GOOD") organisms.

Selective Biocidal Results—refers to the attributes and capabilities of the specific biocidal formulated solutions which eliminate unwanted and/or pathogenic organisms but cause no harm to friendly probiotic organisms Selective Genocide Attributes (SGA)—refers to the attributes and capabilities of the specific biocidal formulated solutions which eliminate only unwanted and/or pathogenic organisms but cause no harm to friendly probiotic organisms Selective Genocide (SG)—refers to the attributes and capabilities of the specific biocidal formulated solutions which eliminate unwanted and/or pathogenic organisms but cause no harm to friendly probiotic organisms Shelf Life and Suspension Stability—means the length of time that the Mini-nanosized Bioavailable Silver Particles maintain their indefinite suspension and biocidal attributes Silver Particle Size—This is the diameter in (mnm) mini-nanometers or (nm) nanometers of bonded silver atoms that have formed a single individual particle that maintains itself as a particle in suspension.

Silver Ion Size—This is the diameter in (mnm) mini-nanometers or (nm) nanometers of silver ions that are in indefinite suspension as a single individual unattached ion that maintains itself as an ion in suspension.

Silver solution—A homogeneous mixture of an aqueous liquid (the solvent) with single solid (mnm) mini-nanometer or (nm) nanometer silver particles (the solute).

Silver Suspension Solvent—An aqueous pure water liquid that holds individual solid mini-nanometer silver particles in suspension.

Specific Formulated and Customized Pure Distilled Aqueous Water Solution—refers to a special specific formulated pure distilled water (containing no toxic chemicals or substances with less than 2 ppm of dissolved solids) solution as a solvent that hosts the biocidal silver particles and ions custom formulated to retard, eliminate, destroy, exterminate, annihilate or kill unwanted fungal pathogenic organisms Specific Formulated Fungal Biocidal Solution—refers to a special specific formulated substance or solution that retards, eliminates, destroys, exterminates, annihilates or kills unwanted fungal pathogenic organisms Specific Formulated Gram Indeterminant Bacterial Biocidal Solution—refers to a special specific formulated substance or solution that retards, eliminates, destroys, exterminates, annihilates or kills unwanted gram indeterminant bacterial pathogenic organisms Specific Formulated Gram Negative Bacterial Biocidal Solution—refers to a special specific formulated substance or solution that retards, eliminates, destroys, exterminates, annihilates or kills unwanted gram negative bacterial pathogenic organisms Specific Formulated Gram Positive Bacterial Biocidal Solution—refers to a special specific formulated substance or solution that retards, eliminates, destroys, exterminates, annihilates or kills unwanted gram positive bacterial pathogenic organisms Specific Formulated Mold Biocidal Solution—refers to a special specific formulated substance or solution that retards, eliminates, destroys, exterminates, annihilates or kills unwanted mold pathogenic organisms Specific Formulated Viral Biocidal Solution—refers to a special specific formulated substance or solution that retards, eliminates, destroys, exterminates, annihilates or kills unwanted viral pathogenic organisms Specific Formulated Fungal Biocidal Substance Solution—refers to a special specific formulated substance or solution that retards, eliminates, destroys, exterminates, annihilates or kills unwanted fungal pathogenic organisms Specific Formulated Gram Indeterminant Bacterial Biocidal Substance Solution—refers to a special specific formulated substance or solution that retards, eliminates, destroys, exterminates, annihilates or kills unwanted gram indeterminant bacterial pathogenic organisms Specific Formulated Gram Negative Bacterial Biocidal Substance Solution—refers to a special specific formulated substance or solution that retards, eliminates, destroys, exterminates, annihilates or kills unwanted gram negative bacterial pathogenic organisms Specific Formulated Gram Positive Bacterial Biocidal Substance Solution—refers to a special specific formulated substance or solution that retards, eliminates, destroys, exterminates, annihilates or kills unwanted gram positive bacterial pathogenic organisms Specific Formulated Mold Biocidal Substance Solution—refers to a special specific formulated substance or solution that retards, eliminates, destroys, exterminates, annihilates or kills unwanted mold pathogenic organisms Specific Formulated Viral Biocidal Substance Solution—refers to a special specific formulated substance or solution that retards, eliminates, destroys, exterminates, annihilates or kills unwanted viral pathogenic organisms Super-Healthy Human Being—measures 9 or above on the patented Scientific Wellness Scales USPTO No. 5692501

Super Healthy Saliva—refers to saliva from a super-healthy human being that has the attributes and capabilities of being lethal only to unwanted and/or pathogenic organisms while causing no harm to friendly probiotic organisms Total Number of Silver Particle Parts Per Million (sp-ppm)—This expression for the total number of individual single unattached (not bonded, combined or related to any other elements) bioavailable pure mini-nanosized or nano-sized silver particles.

Toxic—Means the commonly accepted meaning of anything (substance or element) that causes either short or long-term harm, diseases, death, unwanted chemical Toxic Infectious Condition—refers to a setting where serious and/or dangerous toxic and/or infectious conditions exist in an environmental ecosystem Toxic or Dangerous Infectious Condition—refers to a setting where serious and/or dangerous toxic and/or infectious conditions exist in an environmental ecosystem Sustainable Biologically Balanced Ecological Environment—This expression depicts an ecologically balanced environment in terms of its sustainability over time.

Ultra-Pure Water—refers to a special specific formulated pure steam distilled water (containing no toxic chemicals or substances with less than 2 ppm of dissolved solids) solution as a solvent that hosts the biocidal silver particles and ions custom formulated to retard, eliminate, destroy, exterminate, annihilate or kill unwanted fungal pathogenic organisms Ultra-tiny pure individual silver particles and ions in suspension—refers to the attributes and capabilities of the specific biocidal formulated tiny mini-nanometer silver solutions in suspension in pure water which are lethal only to unwanted and/or pathogenic organisms and cause no harm to friendly probiotic organisms Unattached Pure Silver Particles and Ions—refers to a bioavailable silver particle and/or ion that is a single individual mini-nanosized silver particle or ion that is not bonded, ionized, combined or attached to any other element Uniform steady-state non-clumping formulations—refers to the single bioavailable clear biocidal substance solutions composed of mini-nanosilver particles that stay in suspension indefinitely and do not clump or form larger molecules and/or settle to the bottom of a container Uncontrolled Concentrations—refers to unknown and/or uncontrolled concentrations and numbers of individual colloidal silver particles and ions that could contribute to excessive waste or environmental ecosystem pollutions Unwanted Bacterial Action—refers to unwanted and/or pathogenic bacterial action and changes due to diseases, infections, and/or over population of pathogenic organisms Unwanted Biological Change—refers to unwanted and/or pathogenic biological changes due to diseases, infections, and/or over population of pathogenic organisms Unwanted Chemical Change—refers to unwanted and/or pathogenic chemical changes due to diseases, infections, and/or over population of pathogenic organisms Unwanted Fungal Action—refers to unwanted and/or pathogenic fungal action and changes due to diseases, infections, and/or over population of pathogenic organisms Unwanted Microbial Action—refers to unwanted and/or pathogenic microbial action and changes due to diseases, infections, and/or over population of pathogenic organisms Unwanted Mold Action—refers to unwanted and/or pathogenic mold action and changes due to diseases, infections, and/or over population of pathogenic organisms Unwanted Pathogenic Fungal Growths—refers to dangerous and unwanted population explosions of pathogenic fungi growths Unwanted Pathogenic Gram Indeterminant Growths—refers to dangerous and unwanted population explosions of pathogenic gram indeterminant bacteria growths Unwanted Pathogenic Gram Negative Growths—refers to dangerous and unwanted population explosions of pathogenic gram negative bacterial growths Unwanted Pathogenic Gram Positive Growths—refers to dangerous and unwanted population explosions of pathogenic gram positive bacterial growths Unwanted Pathogenic Mold Growths—refers to dangerous and unwanted population explosions of pathogenic mold growths Unwanted Pathogenic Viral Growths—refers to dangerous and unwanted population explosions of pathogenic viruses Unwanted Viral Action—refers to unwanted and/or pathogenic viral action and changes due to diseases, infections, and/or over population of pathogenic organisms Viral Biocidal Solution—refers to a substance or solution that retards, eliminates, destroys, exterminates, annihilates or kills unwanted viral pathogenic organisms Viral-Destroying, Prophylactic Biocidal Substance Medical Device—means a substance or solution that retards, eliminates, destroys, exterminates, annihilates or kills unwanted pathogenic viral organisms Viral Growths—refers to an explosive growth of viruses in an environmental ecosystem (end of specialized terms in the embodiments/specifications/claims of the invention)

The preceding glossary and definitions of terms used in this application have unique and specialized meanings of both the new terms as well as some terms with different meanings for this application and invention that are used differently from their common general usage in the nanotechnology industry. The following general and common terms related to this application are included herewith having the same meanings as their common general usage in the nanotechnology industry. For anyone with ordinary skills in the art, the present invention uses the general common terms and language as defined in the glossary and set forth herein. It nevertheless should be understood, by a person with experience and expertise in the art, that no limitation of the scope of the invention is hereby intended.

General or Commonly Used Terms Related to Application

Activity coefficient—The activity of a dissolved species in solution is the "effective" concentration of that species ranging from an "ideal" solution to a "real" solution with diminished "activity" due to certain interactions between molecules within the solution.

Adsorption—The formation of a layer of gas, liquid, or solid on the surface of a solid or, less frequently, of a liquid.

Aggregation—Massing of particles/materials together as in clumping.

Aqueous solution—A solution which contains pure water as the solvent.

Coagulation—The process in which colloidal particles come together irreversible to form larger masses. Coagulation can be brought about by adding ions that change the ionic strength of the solution and thus destabilize the colloid.

Compound—A substance formed by the combination of elements in fixed proportions. Compounds, unlike mixtures, cannot be separated by physical means.

Dispersion—The act of scattering or separating; the condition of being scattered, i.e., the incorporation of the particles of one substance into the body of another, comprising colloid solutions.

Elemental silver—This is a scientific term referring to silver in its natural state as a metallic element. The atoms must contain all 47 orbital electrons making the atom complete as a metallic element in its pure state and having no ionic charge.

Flocculation—The process in which particles in a colloid aggregate into larger clumps. Often, the term is used for a reversible aggregation of particles in which the forces holding the particles together are weak and the colloid can be re-dispersed by agitation.

Micron—One millionth of a meter ($10^{-6}$ meter). Also, one micron=1000 nanometers.

Mutual repulsion—A force that disperses silver particles having a like charge. It is the zeta potential that results from adsorbed ions in the solution. In a colloid, mutual repulsion is the force that maintains the stability of the colloid. It is the force that counters the attractive force that would cause flocculation or coagulation.

Nanometer (nm)—A billionth of a meter ($10^{-9}$ meters). A nanometer is the unit of measure used to measure the wavelength of visible light. For example, the thickness of a human hair is approximately 76,200 nanometers or 3 thousandths of an inch. Particles sizes in silver colloids are expressed in nanometers.

Nanoparticle—A solid cluster of atoms.

Oxidation—a chemical reaction characterized by the loss of one or more electrons by an atom or molecule. Originally the term oxidation was used to refer to a reaction in which oxygen combined with an element or compound, e.g., the reaction of magnesium with oxygen to form magnesium oxide or the combination of carbon monoxide with oxygen to form carbon dioxide. When an atom or molecule combines with oxygen, it tends to give up electrons to the oxygen in forming a chemical bond. Such changes are now described in terms of changes in the oxidation number, or oxidation state, of the atom or molecule. Thus oxidation has come to be defined as a loss of electrons or an increase in oxidation number, whether or not oxygen itself is actually involved in the reaction.

Particle size distribution—The distribution of silver particle sizes of a silver colloid solution is determined by a histogram type measurement of the various sizes of silver particles in nanometers and their relative percentages in that solution.

Silver particles—Particles are clusters of silver atoms. The size of the particles found in a colloid can range in size from less than 1 nanometer (nm) to 1000 nm. The size of the particles typically found in silver colloids is under 100 nm. The atoms in a silver particle remain held together by van der Waals' force of attraction that causes like (identical) atoms to be attracted to each other. A particle 1 nm in diameter consists of 31 silver atoms, a particle 10 nm in diameter consists of about 31000 atoms and a particle 20 nm in diameter consists of about 250,000 atoms.

Suspension—A mixture in which small solid particles are suspended in an aqueous liquid.

Turbidity—Cloudiness or opaqueness of water due to suspended silver particles in the water causing a reduction in the transmission of light.

IMPORTANT DISTINCTIVE EMBODIMENTS AND BEST MODE OF THE INVENTION

For a person with ordinary skills in the art, the present invention uses specific terms and language as defined in the glossary and set forth here in the preferred embodiments. It will nevertheless be understood, by a person with ordinary skill in the art, that no limitation of the scope of the invention is thereby intended. Alterations and further modifications of the inventive features set forth herein, and additional applicational methods of the principles of the invention as described herein, which would occur to one skilled in the relevant art and having possession of this disclosure, are to be considered within the scope of the invention. It is also to be understood that the terminology used herein is used for the purpose of explaining and describing the particular restrictive integral, inter-dependent, inter-related and inseparable components and embodiments only. The terms are not intended to be limiting unless specified as such.

These biocidal specialized formulated silver solutions include the common but confusing designation of ppm (parts per million) from 1 to 1,000 ppm for annihilating specific targeted unwanted and/or pathogenic organisms that are used as "specialized exterminator biocidal solutions," cold high-level germ-destroying prophylactic medical devices and other appropriate special applicational uses for pure liquid (aqueous solutions) or atomized (air borne gaseous silver particles and ions produced by a spritzer, atomizer or fogger) in order to reduce or eliminate specific targeted unwanted and/or pathogenic bacterial, viral, fungal, dangerous molds or any other unwanted organisms that include Gram Negative, Gram Positive and Gram-Indeterminant Bacterial Growths, and a multitude of Viruses, Killer Molds and Fungi, (such applicational uses include: sterilization, preservation, disinfection, sanitization, mold eradication and fungus extermination agents).

The present invention is novel, unique and distinct from all other prior art, whether patented or published as educational or marketing information. There are nine key restrictive component embodiments that are integral, inter-dependent, inter-related and inseparable embodiments of this method and invention. All nine when implemented together are important key aspects and components of the advanced technology behind this invention in order to get the desired ideal kill ratios and ideal death curve results and outcomes.

First Restrictive Component Embodiment=Produced by Low Voltage (1)

($1^{st}$ Embodiment) The present invention teaches a customized applicational method where in the very First of the nine key restrictive component embodiments is the primary first restrictive embodiment requirement that the "ideal" tiny and/or small pure single individual bioavailable silver mini-nanoparticles and/or small nanoparticles have only been produced by a low-voltage (>26 v DC current only) manufacturing process that creates the desired mini-nanoparticles and/or nanoparticles according to this invention's specifications. This invention does not teach any applicational methods, preparations or manufacturing processes of colloidal silver nanoparticles, ions and/or compounds (that range in size from 1 nm to 1,000 nm) that have been made, produced or created by a high-voltage (greater than 26 volts DC and/or AC) manufacturing processes. Also, the embodiments of this invention do not teach or include biogenic synthesis of silver nanomaterials or any other recent or sophisticated nanobiotechnologies.

Additionally, the present invention does not include creating silver nanoparticles, ions or a variety of silver compounds through facile synthesis, impregnating biological plants, chemical compounding, biochemical or other biological processes. Furthermore, for a person with ordinary skill in the art, the methods and embodiments of this invention do not include creating or preparing silver nanoparticles, ions or compounds through the use of aqueous solutions of plant extracts as bioreductants.

Second Restrictive Component Embodiment=Produced in Ultra-Pure Water (2)

($2^{nd}$ Embodiment) The present invention teaches a customized applicational method where in the very Second of the nine key restrictive component embodiments is the second restrictive embodiment requirement that the "ideal" tiny and/or small pure single individual bioavailable silver mini-nanoparticles and/or small nanoparticles have been produced in a ultra-pure pharmaceutical grade super-distilled (which is toxic chemical free with less than 2 ppm of dissolved solids) aqueous pure water medium as the solvent solution hosting the "ideal" tiny and/or small pure single individual bioavailable silver mini-nanoparticles and/or small nanoparticles in indefinite suspension. The bioavailable single individual silver mini-nanosized particles and ions (bsimnspi) must be suspended in a solution of super-distilled (less than 2 ppm) aqueous pure water medium, Third Restrictive Component Embodiment=Tiny Sizes of Particle and Ions (3)

($3^{rd}$ Embodiment) The present invention teaches a customized biocidal applicational methods where the Third of the nine key restrictive component embodiments is the smallness of size that yields the best results. Smallness of size is considered the most important of the nine key restrictive component embodiments for discovering, identifying, selecting and producing the desired bioavailable pure silver particles and ions. For unwanted and/or pathogenic organisms, the present invention teaches a customized method to discover, identify, select and produce the "ideal" pure single individual bioavailable mini-nanoparticles and/or nanoparticles that meet the nine restrictive inter-dependent embodiments unique to this method. included in one of the three ranges below. The tiniest first category (3a) ranges from 0.04 mnm to 0.99 mnm, as defined herein. The small second category (3b) ranges from 1.0 nm to 9.9 nm. The third larger category (3c) ranges from 10 nm to 1,000 nm, as set forth herein.

(3a) For tiny unwanted and/or pathogenic organisms, the "ideal size" according to the nine key restrictive component embodiments of this invention for the "ideal" biocidal pure single individual bioavailable silver mini-nanoparticles will be the first and tiniest in silver particle and ion sizes range from: 0.04 mnm to 0.99 mnm; including: 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98 and 0.99 mini-nanometers (mnm) as defined and set forth herein.

These customized biocidal applicational methods will produce antimicrobial solutions that can be implemented in industrial, commercial, medical, hospital, emergency care, educational, forensic, dental, laboratory, office, restaurant, retail, agricultural, embalming, and sports settings as well as public buildings and bathrooms, transportation facilities, resorts, churches, retirement communities, buses, trains, airplanes, automobiles, trucks, swimming pools, salons, spas, military environments and other applicable places.

Research has found that the best results are achieved when the silver particles and ions are clear and smaller than the targeted unwanted and/or pathogenic organisms. This invention teaches a method whereby one skilled in the art can customize and produce a lethal cold high-level (ideal kill ratio>90% as well as with an ideal death curve on contact or in <5 minutes) germ-destroying prophylactic agent for targeted unwanted and/or pathogenic organisms that is totally safe, "green-type," non-toxic and very efficient in a vast number of applicational situations and ecosystems.

The vast majority of applicational uses taught by this invention include using the customized applicational method for discovering, identifying, selecting and producing bioavailable single individual mini-nanosized silver particles and ions (bsimnspi) for testing and evaluation to determine which size of bsimnspi are the ideal size for the applicational method ranging from 0.04 to 0.99 mnm (mini-nanometers) because this size yields the highest percentage kill ratio and the fastest death curve. The perfect ideal size is determined strictly by which size(s) of bioavailable single individual mini-nanosized silver particles and ions (bsimnspi) ultimately and consistently yield the highest percentage kill ratio and the fastest death curve for the desired bioavailable pure silver particles and ions that demonstrate the highest and desired ideal kill ratios and ideal death curves.

Example: In order for a person with ordinary skill in the art to determine the ideal size of bioavailable single individual mini-nanosized silver particles and ions (bsimnspi), three (3) different bsimnsp are selected and tested. The first (1st) size chosen and evaluated can be 0.40 nm, the second (2nd) size can be 0.60 nm, and the third (3rd) size can be 0.90 nm. The size that yields the highest percentage kill ratio and the fastest death curve becomes the chosen ideal size of bioavailable single individual mini-nanosized silver particles and ions (bsimnspi).

Finding the "ideal" size and concentrations of the pure tiny single individual bioavailable mini-nanoparticles and ions will satisfy a person with ordinary skill in the art attempting to discover, identify, select and produce the desired bioavailable pure silver particles and ions that meet the criteria of the nine key restrictive component embodiments. For safely eliminating most targeted unwanted and/or pathogenic organisms (whether bacterial, viral, fungal or mold type of organism) the above implementation of the pure tiny single individual bioavailable mini-nanoparticles and ions will produce the desired biocidal results without causing harm to any living thing or Mother Earth.

However, in order to be comprehensive in this growing field of nanotechnology, the present invention also includes the nine key restrictive component embodiments as possible schemes in the art for ultimately finding the highest and most desired ideal kill ratios and ideal death curves, if and only if larger pure small or larger single individual bioavailable nanoparticles and ions can yield a higher kill ratio, more effective death curve and potent lethal cold high-level germ-destroying prophylactic agent than the ultra-tiny silver particles and ions can do as described above.

It should be understood that the examples of different sizes used herein are used for the purpose of explaining and describing the steps needed to determine the ideal size according to specific embodiments, restrictive integral, inter-dependent, inter-related and inseparable components herein. Particle sizes are analyzed using a high resolution transmission electron microscopy (HRTEM).

(3b) For certain other unwanted and/or pathogenic organisms, the present invention also teaches a customized applicational method for a person with ordinary skill in the art that uses the nine key restrictive component embodiments to discover, identify, select and produce the "ideal" pure small single individual bioavailable silver small nanoparticles that embody higher kill ratios and death curves than the mini-nanosized silver particles and ions.

The "ideal size" for the pure small single individual bioavailable small silver nanoparticles according to the nine key restrictive component embodiments of this invention for the small biocidal pure silver bioavailable nanoparticles will be found in a range in sizes from: 1.0 nm to 9.9 nm; including: 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.6, 9.6, 9.7, 9.8, 9.9 nm in diameter that have produced the desired ideal kill ratios and ideal death curves.

(3c) Though it is unlikely that larger silver particles and compounds can produce more ideal kill ratios and ideal death curves than the mini-nanosized silver particles and ion solutions, the present invention includes the same steps used above to discover, identify, evaluate and produce biocidal solutions. The present invention includes the applicational methods for larger particles and compounds according to the nine key restrictive component embodiments for pure larger silver bioavailable particles/ions in order to enable a person with ordinary skill in the art that wants to discover, identify, select and produce larger silver biocidal agents that have demonstrated significant antimicrobial activity (with the desired ideal kill ratios and ideal death curves) in certain controlled experiments and evaluated environments for larger organisms. A key factor in ascertaining the "ideal" pure single individual bioavailable silver larger nanoparticles includes the combining of both laboratory and field testing according to the inseparable nine key restrictive component embodiments of this invention.

Larger pure single silver nano-particles will range in size from 10.0 nm to 1,000 nm; including: 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, 75.0, 75.5, 76.0, 76.5, 77.0, 77.5, 78.0, 78.5, 79.0, 79.5, 80.0, 80.5, 81.0, 81.5, 82.0, 82.5, 83.0, 83.5, 84.0, 84.5, 85.0, 85.5, 86.0, 86.5, 87.0, 87.5, 88.0, 88.5, 89.0, 89.5, 90.0, 90.5, 91.0, 91.5, 92.0, 92.5, 93.0, 93.5, 94.0, 94.5, 95.0, 95.5, 96.0, 96.5, 97.0, 97.5, 98.0, 98.5, 99.0, 99.5, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 999 1,000 nm (nanometers) in diameter. A key factor in "ideal" pure single individual bioavailable silver nanoparticles includes the combining of both controlled laboratory and carefully administered field tests according to the nine key restrictive component embodiments of this invention. This is done to discover, identify, select and produce any potential biocidal pure silver particle bioavailable activity if the tiny or small pure single silver particles have not produced the desired ideal kill ratios or ideal death curve results.

Additionally, studies have shown that the larger pure silver particles greater than 200 nanometers often have amber, yellow, brown or black coatings on the particles or compounds. When the silver nanoparticles or compounds have gray to black coatings or colors, they are usually not single individual bioavailable silver nanoparticles or ions and they tend to clump into larger particles and settle to the bottom of a container. Typically, the darker the colors are indicative of much larger the silver particles and/or compounds. Darker colors also correlate to reduced bioavailability and diminished biocidal attributes.

Generally, the larger silver particles or silver compounds that range from 10 nanometers to 100 nanometers in size or larger have diminished or reduced surface areas and exhibit weak or poor biocidal activity. Therefore, for most of the applicational methods that are the object of this invention, these larger silver particles or silver compounds are not included because they are not able to satisfy the requirements set forth in the nine key restrictive component embodiments of this invention, due to their severely limited biocidal capabilities and diminished bioavailability.

Fourth Restrictive Component Embodiment=Limited Number of Particles/Ions (4)

($4^{th}$ Embodiment) The Fourth embodiment (which is second in importance) is the total ideal number of bioavailable single individual mini-silver particle and ion parts per million (bsimsppipm) of individual single unattached (not bonded, combined or related to any other element) bioavailable pure mininanosized or nanosized silver particles, according to the disclosed nine key restrictive component embodiments that are inter-dependent, inter-related, integral and inseparable embodiments, as set forth herein.

This invention teaches a custom method of preparing and producing suspended clear bioavailable single individual mini-nanosized silver particles (bsimnsp) that do not clump or sink to the bottom, oxidize or have any colors/coatings ranging from amber to brown to black at room temperatures and ambient atmospheric pressures for pure liquid silver particle and ionic solutions customized with measured concentrations for an ideal number of bioavailable single individual mini-nanosized silver particles and ionic parts per million (bsimnspippm) of bioavailable single mini-nanosized silver particles and ionic parts per liter (bsmnspippl).

Example: In order for a person with ordinary skill in the art to determine the ideal concentration of bioavailable single individual mini-nanosized silver particles and ions (bsimnspi). three different concentrations of bsimnsp are selected and tested. The first (1st) concentration chosen and evaluated can be 5,000 bsimnsp, the second (2nd) concentration can be 15,000 bsimnsp, and the third (3rd) concentration can be 30,000 bsimnsp. The concentration that yields the highest percentage kill ratio and the fastest/shortest death curve becomes the chosen ideal concentration of bioavailable single individual mini-nanosized silver particles and ions (bsimnspi).

It should be understood by a person with ordinary skill in the art that the examples of different concentrations used herein are used for the purpose of explaining and describing the steps needed to determine the ideal concentration according to nine special embodiments and restrictive integral, inter-dependent, inter-related and inseparable components herein.

This ideal concentration correlates to the common designation of 1.0 up to 1000 ppm and any potential dilutions thereof, This total ideal number only includes silver particles and ions and does not include any suspended silver compounds. Both the smallness of size and the ideal number of particles and ions are vital key factors in the applicational methods and embodiments of the present invention, for the following reasons:

a. There is wide spread agreement in the fast growing nanotechnology industry that colloidal silver particles, ions and some silver compounds have proven biocidal (antimicrobial) properties and attributes.

b. The ideal numbers of silver particles and ions are important factors in achieving the desired proven biocidal (antimicrobial) properties and attributes of the bioavailable single individual mini-silver particle and ion parts per million (bsimsppipm) solutions with acceptable ideal kill ratios and ideal death curves as set forth herein. The total ideal number of active silver particles and ions will ultimately determine whether or not the silver solution has sufficient biocidal attributes to satisfy the requirements set forth in the nine key restrictive component embodiments of this invention. A recent article explains why the number of silver particles and ions. See: "PPM" article about the total number of biocidal silver particles in suspension, "Why Higher PPM Is Not Always Better," By Steve Barwick, From: http://thesilveredge.com/ppm.shtml#.VB4VpktCM8

On the other end of the spectrum, it has been discovered that if there are an insufficient number of bioavailable single individual mini-silver particles and ions parts per million (bsimspippm) to annihilate the pathogenic organisms, the pathogens can become stimulated. This is a process called hormesis, where a pathogenic organism has been exposed to a weak or ineffective biocidal agent but is not killed or severely damaged enough to not be able to replicate. When this occurs, the pathogen often replicates faster. One study suggests that it is really the ions which actually flow from the silver nanoparticles when oxidized that actually destroy the pathogenic organisms more than the single individual silver particles. To a lesser degree, the silver particles also have biocidal attributes, but do not appear to be toxic to bacteria in an anaerobic environment. See this recent Article: "ions, not particles, make silver toxic to bacteria," by MIKE WILLIAMS—Jul. 11, 2012; POSTED IN: CURRENT NEWS; http://news.rice.edu/2012/07/11/ions-not-particles-make-silver-toxic-to-bacteria-2/.

c. Yes, it is possible to have too much of a good thing (i.e., in this case, too many of the bsimspippm which (in rare cases) can result in argyria or some other toxic conditions. Too many bioavailable single individual mini-silver particle and ion parts per million (bsimspippm) can cause harmful conditions or create unwanted chemical or biological changes to the eco-system of an organism host, the eco-environment, Mother Earth or worse result in toxic waste. Consequently, this invention teaches a means whereby a person with ordinary skill in the art can discover, identify, select and produce the ideal number of clear bioavailable pure silver particles and ions that can be safely introduced into any environment.

There is a growing concern that the rapid increase in commercial and industrial products containing various nanosized particles, ions or compounds of silver have the potential of contributing to future environmental problems and a decline in innate and acquired immune responses in humans plus cause some environmental pollution problems or toxic waste products. See recent Articles: "In vitro toxicity of silver nanoparticles on murine peritoneal macrophages," PMID_20507217 [PubMed—indexed for MEDLINE]; "Use of nanosilver in consumer products," PMID_22023078 [PubMed—indexed for MEDLINE]; and "Effects of silver nanoparticles on soil enzyme activities," PMID_24115203 [PubMed—indexed for MEDLINE].

d. Some scientists, biochemists, microbiologists, health professionals and medical researchers are aware of the magical yet mystical phenomena that could be called the homeopathic phenomena. Example: In traditional homeopathy, an infinitely small amount/dose of a substance (that causes no harm, toxic waste or unwanted side-effects) either has no effect or creates the desired results. This is contrasted with a massive amount/large dose of the exact same substance that causes serious harm, toxic waste or creates extremely dangerous side-effects. For centuries, this "homeopathic phenomena" has been observed and studied by dedicated scientists, healers and doctors committed to causing no harm.

e. Thus, a homeopathic dosage, amount or number of bsmspippm will have entirely different results or outcomes than a massive number of bsmspippm. See "PPM" article about the total number of bioavailable biocidal silver particles in suspension, "Why Higher PPM Is Not Always Better," By Steve Barwick, From: httplithesilveredge.com/ppm.shtml#.VB4Vp-ktCM8

By including, applying and implementing all of the nine key restrictive component embodiments of this invention, the ideal number of bioavailable single mini-sized or small silver particle and ion parts per million (bsmsspippm) will be determined (including silver ions). This Ideal Number is determined by the number of bsmsspippm that consistently result in the highest ideal kill ratio and ideal death curve and which exhibits selective biocidal results regardless of what the commonly correlated ppm number is determined to be. As set forth herein, the ideal size and Ideal number are far more important determining factors than the conventional ppm.

The "Ideal number of bsmsspippm" will be found in a range from 500 to 10 million silver particles; including: 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, 25,000, 25,500, 26,000, 26,500, 27,000, 27,500, 28,000, 28,500, 29,000, 29,500, 30,000, 30,500, 31,000, 31,500, 32,000, 32,500, 43,000, 43,500, 44,000, 44,500, 45,000, 45,500, 46,000, 46,500, 47,000, 47,500, 48,000, 48,500, 49,000, 49,500, 50,000, 50,500, 51,000, 51,500, 52,000, 52,500, 53,000, 53,500, 54,000, 54,500, 55,000, 55,500, 56,000, 56,500, 57,000, 57,500, 58,000, 58,500, 59,000, 59,500, 60,000, 60,500, 61,000, 61,500, 62,000, 62,500, 63,000, 63,500, 64,000, 64,500, 65,000, 65,500, 66,000, 66,500, 67,000, 67,500, 68,000, 68,500, 69,000, 69,500, 70,000, 70,500, 71,000, 71,500, 72,000, 72,500, 73,000, 73,500, 74,000, 74,500, 75,000, 75,500, 76,000, 76,500, 77,000, 77,500, 78,000, 78,500, 79,000, 79,500, 80,000, 80,500, 81,000, 81,500, 82,000, 82,500, 83,000, 83,500, 84,000, 84,500, 85,000, 85,500, 86,000, 86,500, 87,000, 87,500, 88,000, 88,500, 89,000, 89,500, 90,000, 90,500, 91,000, 91,500, 92,000, 92,500, 93,000, 93,500, 94,000, 94,500, 95,000, 95,500, 96,000, 96,500, 97,000, 97,500, 98,000, 98,500, 99,000, 99,500, 100,000, 105,000, 110,000, 115,000, 120,000, 125,000, 130,000, 135,000, 140,000, 145,000, 150,000, 160,000, 165,000, 170,000, 175,000, 180,000, 185,000, 190,000, 195,000, 200,000, 205,000, 210,000, 215,000, 220,000, 225,000, 230,000, 235,000, 240,000, 245,000, 250,000, 255,000, 260,000, 265,000, 270,000, 275,000, 280,000, 285,000, 290,000, 295,000, 300,000, 305,000, 310,000, 315,000, 320,000, 325,000, 330,000, 335,000, 340,000, 345,000, 350,000, 360,000, 365,000, 370,000, 375,000, 380,000, 385,000, 390,000, 395,000, 400,000, 405,000, 410,000, 415,000, 420,000, 425,000, 430,000, 435,000, 440,000, 445,000, 450,000, 455,000, 460,000, 465,000, 470,000, 475,000, 480,000, 485,000, 490,000, 495,000, 500,000, 505,000, 510,000, 515,000, 520,000, 525,000, 530,000, 535,000, 540,000, 545,000, 550,000, 560,000, 565,000, 570,000, 575,000, 580,000, 585,000, 590,000, 595,000, 600,000, 605,000, 610,000, 615,000, 620,000, 625,000, 630,000, 635,000, 640,000, 645,000, 650,000, 655,000, 660,000, 665,000, 670,000, 675,000, 680,000, 685,000, 690,000, 695,000, 700,000, 705,000, 710,000, 715,000, 720,000, 725,000, 730,000, 735,000, 740,000, 745,000, 750,000, 760,000, 765,000, 770,000, 775,000, 780,000, 785,000, 790,000, 795,000, 800,000, 805,000, 810,000, 815,000, 820,000, 825,000, 830,000, 835,000, 840,000, 845,000, 850,000, 860,000, 865,000, 870,000, 875,000, 880,000, 885,000, 890,000, 895,000, 900,000, 905,000, 910,000, 915,000, 920,000, 925,000, 930,000, 935,000, 940,000, 945,000, 950,000, 955,000, 960,000, 965,000, 970,000, 975,000, 980,000, 985,000, 990,000, 995,000, 1,000,000, 1,010,000, 1,020,000, 1,030,000, 1,040,000, 1,050,000, 1,060,000, 1,070,000, 1,080,000, 1,090,000, 1,100,000, 1,110,000, 1,120,000, 1,130,000, 1,140,000, 1,150,000, 1,160,000, 1,170,000, 1,180,000, 1,190,000, 1,200,000, 1,210,000, 1,220,000, 1,230,000, 1,240,000, 1,250,000, 1,260,000, 1,270,000, 1,280,000, 1,290,000, 1,300,000, 1,310,000, 1,320,000, 1,330,000, 1,340,000, 1,350,000, 1,360,000, 1,370,000, 1,380,000, 1,390,000, 1,400,000, 1,410,000, 1,420,000, 1,430,000, 1,440,000, 1,450,000, 1,460,000, 1,470,000, 1,480,000, 1,490,000, 1,500,000, 1,520,000, 1,540,000, 1,560,000, 1,580,000, 1,600,000, 1,620,000, 1,640,000, 1,660,000, 1,680,000, 1,700,000, 1,720,000, 1,740,000, 1,760,000, 1,780,000, 1,800,000, 1,820,000, 1,840,000, 1,860,000, 1,880,000, 1,900,000, 1,920,000, 1,940,000, 1,960,000, 1,980,000, 2,000,000, 2,020,000, 2,040,000, 2,060,000, 2,080,000, 2,100,000, 2,120,000, 2,140,000, 2,160,000, 2,180,000, 2,200,000, 2,220,000, 2,240,000, 2,260,000, 2,280,000, 2,300,000, 2,320,000, 2,340,000, 2,360,000, 2,380,000, 2,400,000, 2,420,000, 2,440,000, 2,460,000, 2,480,000, 2,500,000, 2,520,000, 2,540,000, 2,560,000, 2,580,000, 2,600,000, 2,620,000, 2,640,000, 2,660,000, 2,680,000, 2,700,000, 2,720,000, 2,740,000, 2,760,000, 2,780,000, 2,800,000, 2,820,000, 2,840,000, 2,860,000, 2,880,000, 2,900,000, 2,920,000, 2,940,000, 2,960,000, 2,980,000, 3,000,000, 3,020,000, 3,040,000, 3,060,000, 3,080,000, 3,100,000, 3,120,000, 3,140,000, 3,160,000, 3,180,000, 4,000,000, 4,020,000, 4,040,000, 4,060,000, 4,080,000, 4,100,000, 4,120,000, 4,140,000, 4,160,000, 4,180,000, 4,200,000, 4,220,000, 4,240,000, 4,260,000, 4,280,000, 4,300,000, 4,320,000, 4,340,000, 4,360,000, 4,380,000, 4,400,000, 4,420,000, 4,440,000, 4,460,000, 4,480,000, 4,500,000, 4,520,000, 4,540,000, 4,560,000, 4,580,000, 5,000,000, 5,050,000, 5,100,000, 5,150,000, 5,200,000, 5,250,000, 5,300,000, 5,350,000, 5,400,000, 5,450,000, 5,500,000, 5,550,000, 5,600,000, 5,650,000, 5,700,000, 5,750,000, 5,800,000, 5,850,000, 5,900,000, 5,950,000, 6,000,000, 6,050,000, 6,100,000, 6,150,000, 6,200,000, 6,250,000, 6,300,000, 6,350,000, 6,400,000, 6,450,000, 6,500,000, 6,550,000, 6,600,000, 6,650,000, 6,700,000, 6,750,000, 6,800,000, 6,850,000, 6,900,000, 6,950,000, 7,000,000, 7,050,000, 7,100,000, 7,150,000, 7,200,000, 7,250,000, 7,300,000, 7,350,000, 7,400,000, 7,450,000, 7,500,000, 7,550,000, 7,600,000, 7,650,000, 7,700,000, 7,750,000, 7,800,000, 7,850,000, 7,900,000, 7,950,000, 7,800,000, 7,850,000, 7,900,000, 7,950,000, 8,000,000, 8,050,000, 8,100,000, 8,150,000, 8,200,000, 8,250,000, 8,300,000, 8,350,000, 8,400,000, 8,450,000, 8,500,000, 8,550,000, 8,600,000, 8,650,000, 8,700,000, 8,750,000, 8,800,000, 8,850,000, 8,900,000, 8,950,000, 9,000,000, 9,050,000, 9,100,000, 9,150,000, 9,200,000, 9,250,000, 9,300,000, 9,350,000, 9,400,000, 9,450,000, 9,500,000, 9,550,000, 9,600,000, 9,650,000, 9,700,000, 9,750,000, 9,800,000, 9,850,000, 9,900,000, 9,950,000, up to 10,000,000 or more of single silver mini-nanosized or nanosized particles.

It should be noted that the Ideal Number of bioavailable single mini-sized or small silver particle and ion parts per million (bsmsspippm) correlates to the conventional misleading but commonly used ppm that is calculated not by the number of particles, ions or compounds in suspension but by the combined weight of colloidal silver particles, ions and compounds in the biocidal solution.

The bsmspippm taught by this invention correlates to the widely used ppm as: 1.0 ppm to 1,000 ppm; including: 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.8.5, 5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, 75.0, 75.5, 76.0, 76.5, 77.0, 77.5, 78.0, 78.5, 79.0, 79.5, 80.0, 80.5, 81.0, 81.5, 82.0, 82.5, 83.0, 83.5, 84.0, 84.5, 85.0, 85.5, 86.0, 86.5, 87.0, 87.5, 88.0, 88.5, 89.0, 89.5, 90.0, 90.5, 91.0, 91.5, 92.0, 92.5, 93.0, 93.5, 94.0, 94.5, 95.0, 95.5, 96.0, 96.5, 97.0, 97.5, 98.0, 98.5, 99.0, 99.5, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 up to 1,000 ppm.

The now widely used ppm is easily misunderstood because it is based upon the total weight of the silver particles, ions and any silver compounds in suspension or resident (clumped) in the aqueous solution due to various size differences. It (ppm) is not based on the actual number of individual single silver particles, compounds, or ions as it also includes any larger clusters or clumps of silver particles or compounds that have settled to the bottom.

Example: The confusion lies in the fact that any solution of silver particles that is designated as 10 ppm, which contains particles whose average size is about 2.0 nanometers will contain about twice as many individual silver particles as a solution (also rated as 10 ppm) where the average size of silver particles are about 4.0 nanometers. See "PPM" article, "Why Higher PPM Is Not Always Better," By Steve Barwick, From: http://thesilveredge.com/ppm.shtml#.VB4Vp-ktCM8

This confusion between the total single number of silver particles in suspension versus the sum total of the weight of all particles, ions and compounds did not exist 15 years ago. In the past, the silver designation of ppm approximated the actual number of single and/or clustered silver particles and compounds suspended as compared to a million molecules of water.

Apparently, as the nanosilver industry has developed smaller and smaller silver particles, including mini-nanosilver particles (as set forth herein), the meaning of it has evolved to include particles, ions and compounds and not just pure single silver particles. In contrast, when you distill water, the ppm therein is solely based on the total number of dissolved solids in the water, not on their total weight.

Fifth Restrictive Component Embodiment=Highest Kill Ratio Possible (5)

($5^{th}$ Embodiment) The Fifth embodiment and vital component of this invention constitutes a consistently high biocidal ideal kill ratio by the bioavailable pure silver mini-nano particles and ions that result in a lethal cold high-level annihilation agent that kills greater than ninety percent (>90%) of the targeted unwanted and/or pathogenic organisms.

Sixth Restrictive Component Embodiment=Best Death Curve Possible (6)

($6^{th}$ Embodiment) The Sixth embodiment is an ideal death curve of the specific targeted organisms (immediately on contact, or in <5 minutes to 24 hrs). The combined "ideal" size and number of single bioavailable silver particles that yield the highest biocidal activity results in the shortest period of time are selected for this invention.

Seventh Restrictive Component Embodiment=Crystal Clear Particles & Ions (7)

($7^{th}$ Embodiment) The Seventh embodiment comprises the absolutely crystal clarity (clear, non-colored particles) of the solutions plus the singularity, individuality and non-clumping attributes of the bioavailable pure mini-nanosized silver particles (including silver ions).

Example: In order for a person with ordinary skill in the art to determine the selective genocide of the bioavailable single individual mini-nanosized silver particles and ions (bsimnspi), a controlled laboratory experiment checks for crystal clearness using state-of-the-art equipment, such as:

scanning electron microscopy (SEM) and high resolution transmission electron microscopy (HRTEM). It is important to frequently check both the ideal number and ideal size of mini-nanosized silver particles and ions (bsimnspi) and pureness of silver i.e., crystal clearness.

When all seven embodiments are satisfied by a person with ordinary skills in the art and the perfect silver bullet biocidal solutions are ready for shipment, it is time to conduct a comparative evaluation of available shipping containers. This can be done easily by evaluating clear glass bottles, dark colored glass bottles and hard plastic bottles to determine which type of bottle best preserves the biocidal properties of said solutions and maintains the integrity and attributes of the specialized formulated biocidal solutions without any loss of quality, contamination or oxidation.

Alterations and further modifications of the inventive features set forth herein, including substitution of other targeted unwanted and/or pathogenic organisms, and additional applicational methods of the principles of the invention as described herein, which would occur to one skilled in the relevant art and having possession of this disclosure, are to be considered within the scope of the invention.

At this point in the use of the methods of this present invention for discovering, identifying, evaluating and producing the perfect biocidal silver bullet for exterminating unwanted and/or pathogenic organisms, a person with ordinary skills in the art will want to conduct actual field tests of the bioavailable single individual mini-nanosized silver particles and ions (bsimnspi) in their normal, ordinary eco-environment to evaluate, ascertain and verify that the bioavailable single individual mini-nanosized silver particles and ions (bsimnspi) are not toxic to any host organisms and/or the natural balances of the eco-environment.

The field studies are designed to make sure that the normal, natural and healthy eco-balance of living organisms has not been upset or negatively altered, and that the biocidal agent is contributing to a sustainable future Mother Earth. Lastly, the field tests are important to ascertain that the bioavailable single individual mini-nanosized silver particles and ions (bsimnspi) will not create or contribute to any type of toxic waste or other environmental problems.

Example: In order for a person with ordinary skill in the art to conduct carefully designed "field studies" using the ideal size(s) and concentration(s) of bioavailable single individual mini-nanosized silver particles and ions (bsimnspi), specific protocols must be followed to maintain the ordinary and natural balances of the ecosystem being evaluated. Each field study needs to be administered by a person with ordinary skill in the art in order to properly test the biocidal attributes of the bioavailable mini-nanosized silver particles and ions that are being evaluated.

Eighth Restrictive Component Embodiment=Selective Genocide Attributes (8)

($8^{th}$ Embodiment) The Eighth critical attribute of the bioavailable pure silver particles is their capability of selective genocide, which means that the silver particles only eliminate, annihilate or kill targeted unwanted and/or pathogenic organisms. Since all silver mini-nanosized and nano-sized particles and ions are completely environmentally safe and harmless to all "good" micro and larger organisms, it is important for anyone skilled in the art to include all of the nine key restrictive component embodiments of this invention, in order to properly discover, identify, select and produce the desired safe green non-toxic bioavailable pure silver particles and ionic solutions set forth herein. The selective genocide component and embodiment of this invention is as important as the predetermined highest ideal kill ratio and ideal death curve described above. This invention teaches laboratory testing of the selective genocide of the ideal size(s) and concentration(s) of the bioavailable single individual mini-nanosized silver particles and ions (bsimnspi) that have been discovered, identified, tested and scientifically determined according to the nine key restrictive component embodiments as integral, inter-dependent, inter-related and inseparable components herein in order to assess their selective genocide capabilities by verifying that the silver particles and/or ions are not harmful to any "good" health enhancing or probiotic organisms.

In order to be sure that the biocidal bioavailable pure silver particles and ionic solutions set forth herein are non-toxic, safe, green-type and be able to positively contribute to a future sustainable ecologically balanced ecosystem, the special selective genocide properties of the silver mini-nanosized and nanosized particles and ions must be tested and confirmed to preserve the biological probiotics that are friendly bacteria promoting healthy digestion and absorption of nutrients as they crowd out pathogens, such as yeasts, other bacteria and viruses that can otherwise cause diseases.

Example: In order to determine the selective genocide of the bioavailable single individual mini-nanosized silver particles and ions, a controlled laboratory experiment must be conducted wherein selected "good" bacteria and friendly probiotic organisms are exposed to and tested against the ideal size(s) and concentration(s) of the bioavailable single individual mini-nanosized silver particles and ions that have been discovered, identified, prepared, tested and scientifically determined to be safe biocidal agents according to the nine key restrictive component embodiments as integral, inter-dependent, inter-related and inseparable components of this invention.

Probiotics (i.e., the "GOOD" micro-organisms) are known for their developing a mutually advantageous symbiosis with the human or animal gastrointestinal tract. The probiotics benefit from the nutritional qualities of foods ingested so the human or animal organism's body will utilize the byproducts of their life processes. Among the thousands of different strains of probiotics, some of the most well-known friendly organisms are: *Acidophilus, Lacto-bacillus, Lacto-bulgaicus, Lacto-plantarum, Lacto-rhamnosus*, Flora, Fauna, *Bifidobacterium Bifidum, B. Infantis, B. Longum, Streptococcus Thermophilis, Enterococcus Faecium*, etc. Probiotics are found in human, animal and plant organisms and are especially important for a sustainable Earth. See Article: "Green synthesis of silver nanoparticles, their characterization, application and antibacterial activity," PMID__ 24157517 [PubMed—indexed for MEDLINE].

Another example of selective genocide comes from an unpublished scientific study in the 1970s and 1980s where the ideal kill ratios and ideal death curves of several commercially available mouth rinses and washes was compared to the healthy saliva of 16,000+ participants, who qualified as super-healthy human beings. The stringent definition and qualifying criteria for a super-healthy human being was defined and limited to the participants in the large study that were individuals that could meet the following minimum standards, with verifiable evidence of all of the following:

(1) better than normal resting heart rates (RHRs) and blood pressures (BPs);
(2) had not used any commercial mouth rinses/washes or taken any prescription medicines in the same 10 years for any disorder or disease conditions;
(3) had no need for and were not currently on any prescribed medicines;

(4) had not experienced even a minor cold or flu condition in over 10 years;
(5) had not had any minor or major surgeries in over 10 years (except for minor sports injury repairs);
(6) experienced normal sleeping patterns without any insomnia;
(7) did not have any dental work or pains, tooth aches or decay in over 10 years;
(8) had not been to a dentist for any reason in over 10 years; and,
(9) had normal healthy relationships and emotional stability.

The outcomes of this carefully timed dental and biological study were quite surprising to the dentists, scientists and medical researchers. As expected, the mouth rinses and washes killed most or all "good" and "bad" organisms and pathogens when exposed to the manufactured product. Some commercial products with the higher concentrations of toxic chemicals had faster kill ratios than the more diluted ones.

The shocking outcomes of this study, though, were the unexpected much faster (death curves) and more complete kill ratios of the super-healthy salivas from the super-healthy human beings. With no exceptions, the super-healthy salivas quickly and completely annihilated all of the pathogenic organisms at least 70% faster than the best and highly concentrated yet toxic mouth rinses or washes.

The biggest surprise, however, was the selective genocide of the super-healthy salivas. The super-healthy salivas did not harm, annihilate, kill or destroy any of the "good" probiotic organisms when they were exposed to the super-healthy salivas' genocidal attributes. The "good" probiotic organisms tested included those most commonly found in a healthy mouth, including all "good" micro and larger bacteria and organisms, *acidophilus, lacto-bacillus, lacto-bulgaicus, lacto-plantarum, lacto-rhamnosus*, flora, fauna, *bifidobacterium bifidum, B. Infantis, B. Longum, streptococcus themophilis, enterococcus faecium*, digestive enzymes, and especially the biological probiotics that are the friendly bacteria promoting healthy digestion and absorption of nutrients.

When exposed to the super-healthy salivas, the probiotic organisms remained unharmed, unaffected and slightly more active than usual apparently looking for missing pathogenic organisms to crowd out of the healthy mouth's eco-environment that were annihilated by the super-healthy salivas. The study also included the comparative salivas of over 826,400 other individuals that regularly used commercial mouth rinses and washes to sweeten their breath (widely advertised and promoted as the best socially acceptable behaviors using the popular perfumed mouth rinses and washed) according to the common so called proper etiquette behaviors and the widely advertised social pressures which had been influenced by the financially supported "fashion police" and the commercial manufactures spending large amounts of money advertising of their sterilizing products. Apparently there is a lack of comparative research studies into the frequency of colds, flu symptoms and sinus infections that could be associated with or caused by frequent use of the commercial sterilizing products. Doing a PubMed or MEDLINE search will verify this lack of correlative studies.

Interestingly enough, most of the study participants who regularly used mouth rinses and washes also had a long history of repeated cases of sore throats, flu symptoms and chronic sinus infections. Some of the researchers suspected there might be a strong correlation between the symptoms and the regular use of the sterilizing products, but decided to put further studies of this off for a future time. Since this data was interesting (to the team of medical, scientific and dental researchers) but not the main objective of the team did not choose to further examine the potential and reasonable connections and correlations that existed between the annihilation of all microorganisms (both the good and the bad bacteria) by the commercially manufactured biocidal mouth rinses and washes which left behind a temporary unbalanced ecological environment in the individual's mouth where the pathogenic bacteria could grow unchecked and uninhibited and thus be able to grow exponentially without any of the good bacteria slowing down their population explosion and growth curve.

The researchers did study which type of pathogenic disease causing micro-organisms were the first organisms to populate the sterile ecosystem in the sterilized mouth, and found out that without exception, it was the pathogenic organisms that were the quickest ones to recover and repopulate after being exposed to the antimicrobial genocide solutions of the mouth rinses and washes. It was these pathogenic organisms that quickly invaded the temporary sterile conditions in the mouth, now that there were no probiotic organisms to crowd them out or retard their replication processes.

The team of researchers also verified that it took a much longer period of time for the more fragile and good probiotic organisms to repopulate a sterilized mouth. This important study was never published, however, due to the self-serving economic interests and political agendas of the dental industry which profited greatly from the commercial products.

Other research studies suggest that the bioavailable pure silver mini-nano particles and ions appear to function much like the sophisticated immuno activity of the white blood cells, such as the NK White Blood Cells which invade pathogens and destroy them from the inside of the cell as part of their Immunocompetency Functioning (as defined herein). The NK White Blood Cells are known to selectively target only unwanted or pathogenic organisms for annihilation, providing the immune system components (composed of T-Cells, B-Cells and NK-Cells) are in a healthy and balanced condition and not in crisis.

Many Natural and Homeopathic Medicines are also known to contribute to or possess selective genocide attributes causing no unwanted harm or dangerous side-effects. As more and more resistant strains of pathogenic organisms are discovered, the future importance of non-toxic, safe, green-type proven effective biocidal agents that have selective genocide attributes causing no harm will dramatically increase.

Ninth Restrictive Component Embodiment=Contributes to Sustainable Future (9)

($9^{th}$ Embodiment) The Ninth embodiment is best described as the biocidal applicational use of the silver particles must maintain a healthful, safe, sustainable biologically balanced ecological environment in both the host and in the surrounding eco-environment. This means that the biocidal actions of the tiny or minute silver particles will create trash to be disposed of naturally but will not create any toxic waste products, toxic chemical residues or dangerous side-effects or infectious conditions or other toxic substances that must be carefully handled or disposed of with great caution.

A scientist from a colloidal silver product manufacturing company claims that "Silver Nanoparticles: No Threat to the Environment," by George J. Maass, Ph.D. (Colloidal Science Laboratories), https://www.purestcolloids.com/Silver-NoThreat.pdf. This new area of concern in the nanotechnology field needs further studies to actually determine what affects the many silver particles of different sizes and combinations with other compounds will have on an ecosystem.

Example: In order for a person with ordinary skill in the art to evaluate the stability and shelf life of the bioavailable mini-nanosized silver particles and ions, a potency study needs to be done which periodically assesses any negative changes or losses in the biocidal properties and attributes of the mini-nanosized silver particle and ionic solutions. This also includes customizing the specialized formulated solutions for specific targeted unwanted and/or pathogenic organisms, specific sizes and concentrations of the silver particles and ions that have been selected according to the schemes set forth herein.

The present invention uses pure super-tiny silver particles and ions as the only active biocidal ingredients and its stand-alone exterminating properties with proven killing abilities against unwanted and/or pathogenic organisms that may cause disease, pain, death, decomposition, decay, discoloration and/or deterioration. For best results, the silver particles and ions are not combined, synthesized or associated with any other elements or agents because this significantly reduces both their measured kill rations and calculated death curves.

The present invention is directed to using only single mini-nano-sized bioavailable metallic silver elements (and silver ions) in totally sterile, water based solutions. Each solution is composed of stand-alone, mini-nano-sized silver particles that can attach to a carrier (like a pure water particle), travel over a distance (naturally or by force), and then engage and destroy on contact all forms of unwanted and/or pathogenic organisms that may cause disease, pain, death, decay, discoloration, decomposition and/or deterioration in humans, animals, commercial products and/or their environments. It is stable with a long shelf life. The invention can be widely implemented as a safe, "green-type," non-toxic single independent silver particle (mini-nano-sized) and ionic solution in distilled water of maximum purity that is useful as a biocidal medical device.

The present invention consists of unique applicational methodologies and modes for preparing and producing as well as complete customized methods for implementing and using safe "green-type" non-toxic liquid specific formulated mini-nano-sized silver particle and ionic non-clumping biocidal substance solutions that can be used as organic solutions to eradicate unwanted and/or pathogenic organisms, preserve sterile conditions and forestall or prevent unwanted infectious causing or contaminating chemical and biological changes or microbial/bacterial actions, plus retard deterioration and decomposition or unacceptable negative changes. These formulated customized biocidal applications have anti-microbial properties and are designed to be used against targeted unwanted and/or pathogenic organisms, or as sterilizers or embalming medical devices that can significantly retard the carious destructive processes of nature.

These biocidal applications are comprised of specially formulated mini-nano-sized silver particles (about 0.04-0.99 mini-nano-meters in size) in sterile liquefied stable suspended preparations. Additionally, these specific formulated customized biocidal applications may be added (as a healthy safe non-toxic preservative) to food and/or drink products. These specially formulated customized mini-nano-scopic solutions and mixtures contain electrically charged mini-nano-particles and ions of pure silver with a fineness of 0.999+ purity in complete stable suspension and uniform steady-state non-clumping formulations.

The invention provides precise formulations and protocols of discovering, identifying, evaluating, producing and manufacturing processes that will result in controlled ultra-refined mini-nano-sized uniform silver particles and ions necessary to satisfy the technological requirements of the nine key restrictive component embodiments of this invention in order to produce safe liquid customized solutions that can be used as anti-microbial, biocidal and germicidal agents to exterminate unwanted and/or pathogenic organisms.

The present invention provides comprehensive schemes and procedures for the preparation, production and customized applications which utilize safe "green-type" non-toxic liquid formulated mini-nano-sized silver non-clumping particles in solutions. The specific prepared customized applications are designed to be used as biocidal agents and medical devices that can significantly retard the carious destructive processes of nature as well as have positive anti-microbial properties comprised of specially formulated customized mini-nano-sized silver particles in sterile liquefied stable suspended preparations. The biocidal methods take advantage of existing technology based equipment by using customized design procedures, precise formulations and protocols of custom-made methods and procedures for discovering, identifying, evaluating, testing, producing and manufacturing processes that will result in controlled tiny ultra-refined mini-nano-sized uniform silver particles/ions necessary for the specially formulated customized liquid ideal biocidal solutions.

In accordance with the present invention, the distilled water aqueous solution has less than 2 ppm (parts per million) or less of inert dissolved solids, with no toxic substances, chemical or residues whatsoever included. The mini-nano-sized particles of pure silver are about 0.04-0.99 nanometers in size. The silver is at least 99.9999% pure. The ideal concentrations range from 1,000 to 10 million single bioavailable mini-nano-sized silver particles and ions or the commonly used concentrations of 0.5 ppm to 1,000 ppm.

Exemplary Scheme Using the Nine Key Restrictive Component Embodiments

The following Example is provided to enable any person with ordinary skills in the art to make and use the invention and sets forth the best modes contemplated by the inventor of carrying out his invention in order to discover, identify, evaluate and produce the ideal sizes and concentrations of bioavailable single individual mini-nanosized silver particles and ions (bsimnspi). so they can be used according to the present invention's embodiments in order to create a safe non-toxic "green-type" potent eco-friendly biocidal agent. The steps are sequential and easy to follow.

The first step ($1^{st}$) is to acquire ultra-pure distilled water with no chemical contaminants and less than 2 ppm of dissolved solids. The purity of the water is very important. Most deionized and/or multiple filtered waters are not pure enough for this application.

The second step ($2^{nd}$) is to use an existing low-voltage DC (which means less than 26 volts) colloidal silver generator that is capable of producing a tiny ideal size of bioavailable single individual mini-nanosized silver particles and ions (bsimnspi) that range in size from 0.4 mini-nanometers (mnm(to 0.9 mnm. Silver generators that use higher than 26 volts DC (or AC of any voltage) are not used in the scheme of this invention and are not included in the preferred embodiments, because they produce much larger and often colored or coated silver particles, ions and compounds than the low voltage generators. It is recommended that a person with ordinary skills in the art avoid any voltages such as:110 volts, 220 volts, 440 volts, 1,000 volts, 10,000 volts or 20,000 volts (whether AC or DC). It should be noted that all silver generators produce a variety of sizes of the colloidal silver particles and ions, regardless of voltages used.

The third step ($3^{rd}$) is comprised of taking the already produced tiny particles and ions of the previous second step in which the ideal size of the particles and ions has been determined according to the third component embodiment. For this example, the ideal sizes of tiny silver particles were found within the range from 0.4 nmn to 0.7 nmn. Thus, the logical next step is to create at least three different concentrations (or more) of the bioavailable single individual mini-nanosized silver particles and ions (bsimnspi) so that laboratory assessments and tests can be conducted in accordance with the nine key restrictive component embodiments of this invention. The purpose of this third step is to discover the ideal concentration, i.e., the ideal number as well as the ideal sizes of silver particles in solution that results in the highest kill ratio and death curve. During the third step ($3^{rd}$), the evaluation of 3 different concentrations of the ideal sized silver particles and ions will result in finding the ideal biocidal solution as a customized and specialized formulated solution.

When the ideal biocidal solution is exposed in a controlled laboratory setting to specific targeted unwanted and/or pathogenic organisms, the results will determine the ideal biocidal attributes according to which concentrations and total number of bioavailable single individual mini-nanosized silver particles and ions (bsimnspi) yield the highest kill ratio and the fastest and most complete death curve. A person with ordinary skills in the art will thus be able to find the perfect biocidal silver bullet for any targeted unwanted and/or pathogenic organisms.

For this example, the ideal concentrations that yielded the highest kill ratios and the best death curves in the third step upon exposure to the test pathogens in the lab were determined to fall in a range between 20,000 to 2 million single individual silver particles and ions per liter. This then becomes the ideal particle sizes and concentrations for further assessing the ideal biocidal solution to see if it can qualify as a selective genocide biocidal substance, which comprises the next step (#4). Completing the third step will result in determining the combination of both the ideal sizes and ideal number (concentrations) of the suspended bioavailable single individual mini-nanosized silver particles and ions that have been prepared according to the specifications set forth herein.

Upon completion of this third step, a person with ordinary skills in the art will have produced a customized and specialized formulated solution that meets the criteria of the first six of the nine key restrictive component embodiments. This renders the ideal biocidal solution ready for the next step so that it can now be evaluated for the Seventh ($7^{th}$) Embodiment which is selective genocide for a safe, non-toxic, clear silver biocidal solution. Once the ideal biocidal attributes have been discovered, identified, evaluated and verified according to the specifications, the fourth step ($4^{th}$) is to conduct laboratory tests with the ideal biocidal solution which was prepared according to the schemes and embodiments of the present invention by exposing it to a variety of known "good" probiotic bacteria and friendly organisms according to the specifications set forth herein. This turns out to be a very important step for the ideal biocidal solution to determine and verify that it possesses the important attribute of "selective genocide/" This key attribute is one of the preferred embodiments of this invention that sets the art apart from all other biocidal substances and solutions.

After the "selective genocide" attribute has been validated, the fifth step ($5^{th}$) is to conduct a series of field tests using the ideal biocidal solution that has been prepared according to the schemes and embodiments set forth herein by testing the ideal biocidal solution in the actual settings and environments where the targeted unwanted and/or pathogenic organisms are usually found. This means conducting controlled tests in the normal environments and habitats of the targeted organisms. This includes such organisms that commonly reside within a host (such as an animal or human body), or live within certain structures such as: trains, commercial and office buildings, hotels, airplanes, vehicles, health care facilities, gyms, spas, homes, restaurants, markets, pools, etc. The purpose of the field test is to verify that the ideal biocidal solution of bioavailable single individual mini-nanosized silver particles and ions (bsimnspi) is safe, non-toxic, "green-type" eco-friendly and contributes to a future sustainable eco-environment. The field testing of the specialized formulated solutions is another embodiment that sets this invention apart from all others.

When all of the above five steps are completed, a person with ordinary skill in the art is now ready to produce larger quantities or batches of the tested and verified specialized formulated solutions for use against specific targeted unwanted and/or pathogenic organisms. The next step, the sixth step ($6^{th}$) comprises the production for use of the verified specialized formulated solutions in the specific environments and settings where the unwanted and/or pathogenic organisms are commonly found.

For this example, in both the laboratory settings and the field tests, the ideal biocidal solution could be appropriately implemented as an exterminating medical device or environmental improvement agent by its application as a lethal cold high-level (ideal kill ratio>90% as well as with an ideal death curve on contact or in <5 minutes) germ-destroying prophylactic agent for targeted unwanted and/or pathogenic organisms. The invention has successfully proven itself to be an ideal biocidal agent solution against many dangerous or deadly gram positive, negative and indeterminant bacteria, viruses, molds and fungi.

These include the following unwanted and pathogenic organisms, and more:

Gram Positive Bacteria—Including: *Actinobacteria, Actinomyces, Actinomyces georgiae, Actinomyces gerencseriae, Actinomyces israelii, Bacillales, Bacillus, Bacillus mojavensis, Bacillus weihenstephanensis, Clostridium, Clostridium acetobutylicum, Clostridium aerotolerans, Clostridium argentinense, Clostridium autoethanogenum, Clostridium baratii, Clostridium beijerinckii, Clostridium bifermentans, Clostridium botulinum, Clostridium butyricum, Clostridium cadaveris, Clostridium cellobioparum, Clostridium cellulolyticum, Clostridium cellulovorans, Clostridium chauvoei, Clostridium clostridioforme, Clostridium colicanis, Clostridium difficile, Clostridium estertheticum, Clostridium fallax, Clostridium formicaceticum, Clostridium histolyticum, Clostridium innocuum, Clostridium kluyveri, Clostridium ljungdahlii, Clostridium novyi, Clostridium paradoxum, Clostridium paraputrificum, Clostridium clostridioforme, Clostridium colicanis, Clostridium difficile, Clostridium estertheticum, Clostridium fallax, Clostridium formicaceticum, Clostridium histolyticum, Clostridium innocuum, Clostridium kluyveri, Clostridium ljungdahlii, Clostridium novyi, Clostridium paradoxum, Clostridium paraputrificum, Clostridium perfringens, Clostridium phytofermentans, Clostridium piliforme, Clostridium ragsdalei, Clostridium ramosum,*

*Clostridium saccharobutylicum, Clostridium saccharoperbutylacetonicum, Clostridium scatologenes, Clostridium septicum, Clostridium sordellii, Clostridium sporogenes, Clostridium stercorarium, Clostridium sticklandii, Clostridium straminisolvens, Clostridium tertium, Clostridium tetani, Clostridium thermosaccharolyticum, Clostridium tyrobutyricum, Clostridium uliginosum, Corynebacterium, Corynebacterium amycolatum, Corynebacterium bovis, Corynebacterium diphtheriae, Corynebacterium efficiens, Corynebacterium granulosum, Corynebacterium jeikeium, Corynebacterium macginleyi, Corynebacterium minutissimum, Corynebacterium renale, Desulfitobacterium dehalogenans, Enterococcus, Fervidobacterium changbaicum, Fervidobacterium gondwanense, Fervidobacterium islandicum, Georgenia ruanii, Lactobacillales, Listeria, Listeriaceae, Microbispora corallina, Nocardia, Nocardia asteroides, Nocardia brasiliensis, Nocardia farcinica, Nocardia ignorata, Pasteuria, Propionibacterium acnes, Rhodococcus equi, Sarcina* (genus), *Solobacterium moorei, Sporosarcina, Sporosarcina aquimarina, Sporulation in Bacillus subtilis, Staphylococcus, Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus muscae, Staphylococcus nepalensis, Staphylococcus pettenkoferi, Staphylococcus pseudintermedius, Staphylococcus saprophyticus, Staphylococcus schleiferi, Staphylococcus succinus, Staphylococcus warneri, Staphylococcus xylosus, Strangles, Streptococcus, Streptococcus agalactiae, Streptococcus anginosus, Streptococcus bovis, Streptococcus canis, Streptococcus downei, Streptococcus faecalis, Streptococcus gordonii, Streptococcus iniae, Streptococcus lactarius, Streptococcus mitis, Streptococcus mutans, Streptococcus oralis, Streptococcus parasanguinis, Streptococcus peroris, Streptococcus pneumoniae, Streptococcus pyogenes, Streptococcus ratti, Streptococcus salivarius, Streptococcus sanguinis, Streptococcus sobrinus, Streptococcus suis, Streptococcus thermophilus, Streptococcus tigurinus, Streptococcus uberis, Streptococcus vestibularis, Syntrophomonas curvata, Syntrophomonas palmitatica, Syntrophomonas sapovorans, Syntrophomonas wolfei, Syntrophomonas zehnderi,* and *Viridans streptococci.*

Gram Negative Bacteria—Including: *Acetic acid bacteria, Acinetobacter baumannii, Agrobacterium tumefaciens, Anaerobiospirillum, Anaerolinea thermolimosa, Anaerolinea thermophila, Arcobacter, Arcobacter skirrowii, Armatimonas rosea, Bacteroides, Bacteroides fragilis, Bacteroides ruber, Bartonella japonica, Bartonella koehlerae, Bartonella taylorii, Bdellovibrio, Brachyspira, Caldilinea aerophila, Cardiobacterium hominis, Chaperone-Usher fimbriae, Chthonomonas calidirosea, Coxiella burnetii, Cyanobacteria, Cytophaga, Dialister, Enterobacter, Enterobacter cloacae, Enterobacter cowanii, Enterobacteriaceae, Enterobacteriales, Escherichia, Escherichia coli, Escherichia fergusonii, Fimbriimonas ginsengisoli, Fusobacterium necrophorum, Fusobacterium nucleatum, Fusobacterium polymorphum, Haemophilus felis, Haemophilus haemolyticus, Haemophilus influenzae, Haemophilus pittmaniae, Helicobacter, Helicobacter pylori, Klebsiella pneumoniae* and *oxytoca, Kluyvera ascorbata, Kluyvera cryocrescens, Kozakia baliensis, Legionella, Legionella pneumophila, Leptotrichia buccalis, Levilinea saccharolytica, Luteimonas aestuarii, Luteimonas aquatica, Luteimonas composti, Luteimonas lutimaris, Luteimonas marina, Luteimonas mephitis, Luteimonas vadosa, Megamonas, Megasphaera, Meiothermus, Methylobacterium fujisawaense, Morax-Axenfeld diplobacilli, Moraxella, Moraxella bovis, Moraxella osloensis, Morganella morganii, Negativicutes, Neisseria cinerea, Neisseria gonorrhoeae, Neisseria meningitidis, Neisseria sicca, Nitrosomonas eutropha, Nitrosomonas halophila, Nitrosomonas oligotropha,* OMPdb, *Pectinatus, Pelosinus, Pontiac* fever, *Propionispora, Proteobacteria, Proteus mirabilis, Proteus penneri, Pseudomonas, Pseudomonas aerugio/nosa, Pseudomonas genome database, Pseudomonas luteola, Pseudoxanthomonas broegbernensis, Pseudoxanthomonas japonensis, Rickettsia rickettsii, Salmonella, Salmonella bongori, Salmonella enterica, Salmonella enterica* subsp. *enterica, Samsonia, Selenomonadales, Serratia marcescens, Shigella, Sorangium cellulosum, Sphaerotilus, Spirochaeta, Spirochaetaceae, Sporomusa, Stenotrophomonas, Stenotrophomonas nitritireducens, Thermotoga neapolitana, Trimeric autotransporter adhesin, Vampirococcus, Verminephrobacter, Vibrio adaptatus, Vibrio azasii, Vibrio campbellii, Vibrio cholerae, Vitreoscilla, Wolbachia,* YadA bacterial adhesin protein domain, and *Zymophilus.*

Gram Indeterminant Bacteria—Including: Amphitrichous, Anthrax Bacilli, Atrichous, Borellia, Cervical Lymphadenitis, Chlamydiae, Chloroflexi, Chrysiogenetes, Deinococcus-Thermus, Dictyoglomi, Diphtheria, Drug Multi-Resistant-Tuberculosis/Cellulitis, Elusimicrobia, Endospores, Fibrobacteres, Firmicutes, Gemmatimonadetes, Hepatitus B, Heterotrophic, Lentisphaerae, Lupus Vulgaris, Osmophiles, Nitrospira, *Nocardia Asteroides*, Papulonecrotic Tuberculid, Pericarditis, Planctomycetes, Synergistetes, Tenericutes, Tetanus, Treponema, and Tuberculoid and Histoid Leprosy, Urogenital Tuberculosis, and Verrucomicrobia.

Viruses—Including: Cryptococcus gattii, Enterovirus, Orthomyxoviridae, Piconavirus, coronavirus, Rhinovirus, and Rotovirus, norovirus.

Molds—Including: Alternaria, Aspergillus, Cladosporium, Penicillium, Stachybotrys chartarum, and Trichoderma harzianum.

Fungi—Including: Candida albicans, Candida parasilosis, Histoplasma capsulatum, Crytococcus neoformans, Coccidioides (valley fever), Dermatophyte (Atheletes foot), Exserohilum rostratum, There are no examples of prior art that embody the combination of technologies behind this invention or use all of the nine key restrictive component embodiments set forth herein. All other prior art and patents have different sizes, uncontrolled concentrations or use silver as an ingredient combined with other ingredients to form compounds. There are no instances of any prior art that teach the use of mini-nanometer (mnm) silver particles and ions combined with the nine preferred embodiments of this invention.

In many of the published medical studies in the rapidly growing nanotechnology industry (that could be considered as prior art), the biocidal attributes depend solely on the total combined killing efficacy of all ingredients after they are combined into a composition. It is unlikely that any of the prior art has any application capabilities or stand-alone pathogenic killing efficacies comparable to the present more simple invention because of the losses in biocidal efficiencies of the silver colloids due to their combinations with other elements and/or ingredients. Those that do teach a non-technical laymen's use of the tiny silver particles at 0.0008 microns (i.e., 0.8 nanometers) suggest large, unknown concentrations of sliver particles and ions that range in numbers from a few thousand to 5 million, but this art cannot qualify for the stringent requirements set forth in the nine key restrictive component embodiments. See The Silver Edge Articles @ http://www.thesilveredge.com/ or, http://thesilveredge.com/ppm.shtml#.VB4Vp-ktCM8.

Taken all together, the inseparable distinctive embodiments of this art are the essential components of this customized method and invention. While the invention has been described with reference to certain preferred customized embodiments, those skilled in the art will appreciate that various modifications, changes, omissions, and substitutions that can be made without departing from the spirit or technologies of the nine key restrictive component embodiments of this invention. It is therefore intended that the invention be limited only by the scope of the appended claims.

BRIEF DESCRIPTION OF DRAWINGS

The invention is described in greater detail in the following description of an example embodying the best mode of the invention, taken in conjunction with the drawing figures, in which:

FIG. 1 is a block diagram illustrating a preferred form of the invention.

FIG. 2 is a complete schematic diagram showing the methodologies of the customized manufacturing processes of the methods according to the invention's nine embodiments and the procedural protocols of the various customized design aspects of the invention.

Figure 3:
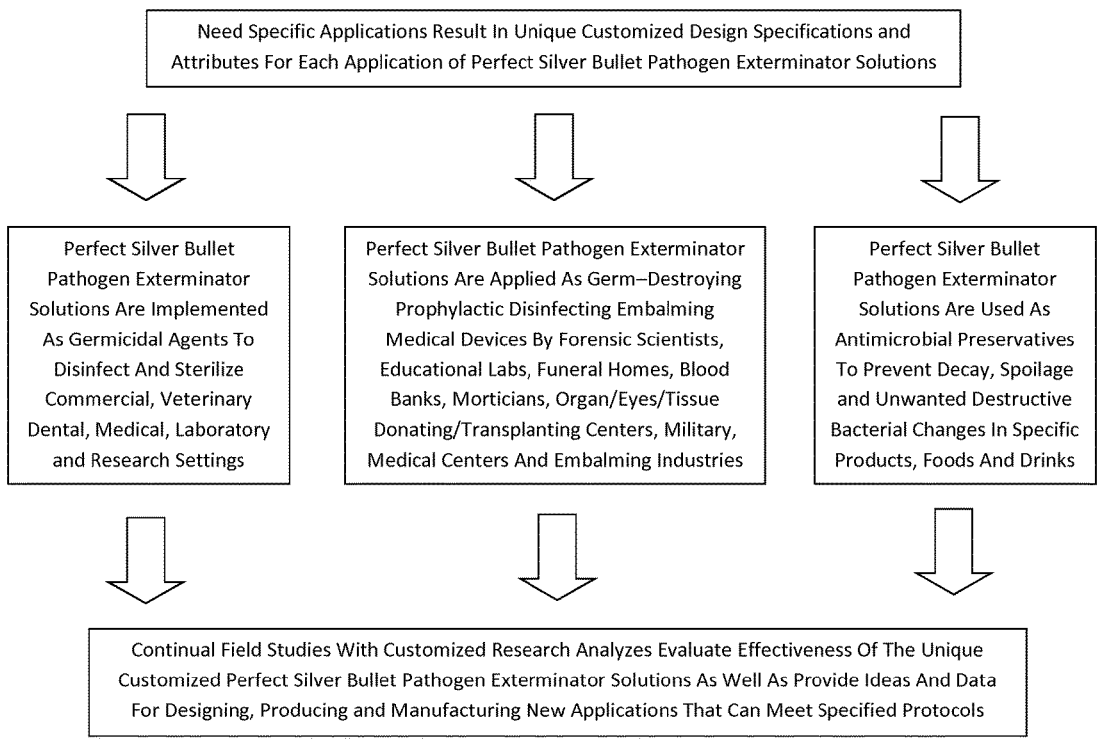
FIG. 3 is a comprehensive schematic diagram showing the applications, uses and fields of the invention and the procedural protocols of the various facets of the invention.

What is claimed is:

1. A method of preparing and producing non-toxic liquid specific formulated biocidal substance solutions that can be used to reduce or eliminate pathogenic gram positive bacterial growths and/or retard the effects of pathogenic gram positive bacteria, the method comprising the steps of: a) creating at least one scheme for the preparation and production of the non-toxic liquid solutions for biocidal application against gram positive bacteria; and b) using the scheme to prepare and produce specific formulated gram positive bacterial biocidal solutions comprising colloidal silver particles and ions in pure distilled aqueous water solution with less than 2 ppm of dissolved solids, wherein the colloidal silver particles are prepared using a voltage, the voltage is 26 volts DC or less, the colloidal silver particles have a particle size of between 0.4 nm and 0.7 nm, and either (i) the number of unattached pure silver particles and ions are from 100,000 to 1 million, or (ii) the concentration of unattached pure silver particles and ions is from 0.5 ppm to 5 ppm, the biocidal solutions thus made are effective to reduce or eliminate pathogenic gram positive bacterial growths and/or retard the effects of pathogenic gram positive bacteria.

2. A method of preparing and producing non-toxic liquid specific formulated biocidal substance solutions that can be used to reduce or eliminate pathogenic gram negative bacterial growths and/or retard the effects of pathogenic gram negative bacteria, the method comprising the steps of: a) creating at least one scheme for the preparation and production of the non-toxic liquid solutions for biocidal application against gram negative bacteria; and b) using the scheme to prepare and produce specific formulated gram negative bacterial biocidal solutions comprising colloidal silver particles and ions in pure distilled aqueous water solution with less than 2 ppm of dissolved solids, wherein the colloidal silver particles are prepared using a voltage, the voltage is 26 volts DC or less, the colloidal silver particles have a particle size of between 0.4 nm and 0.7 nm, and either (i) the number of unattached pure silver particles and ions are from 100,000 to 1 million, or (ii) the concentration of unattached pure silver particles and ions is from 0.5 ppm to 5 ppm, the biocidal solutions thus made are effective to reduce or eliminate pathogenic gram negative bacterial growths and/or retard the effects of pathogenic gram negative bacteria.

3. A method of preparing and producing non-toxic liquid specific formulated biocidal substance solutions that can be used to reduce or eliminate pathogenic gram indeterminate bacterial growths and/or retard the effects of pathogenic gram indeterminate bacteria, the method comprising the steps of: a) creating at least one scheme for the preparation and production of the non-toxic liquid solutions for biocidal application against gram indeterminate bacteria; and b) using the scheme to prepare and produce specific formulated gram indeterminate bacterial biocidal solutions comprising colloidal silver particles and ions in pure distilled aqueous water solution with less than 2 ppm of dissolved solids, wherein the colloidal silver particles are prepared using a voltage, the voltage is 26 volts DC or less, the colloidal silver particles have a particle size of between 0.4 nm and 0.7 nm, and either (i) the number of unattached pure silver particles and ions are from 100,000 to 1 million, or (ii) the concentration of unattached pure silver particles and ions is from 0.5 ppm to 5 ppm, the biocidal solutions thus made are effective to reduce or eliminate pathogenic gram indeterminate bacterial growths and/or retard the effects of pathogenic gram indeterminate bacteria.

4. A method of preparing and producing non-toxic liquid specific formulated biocidal substance solutions that can be used to reduce or eliminate pathogenic viruses bacterial growths and/or retard the effects of pathogenic viruses, the method comprising the steps of: a) creating at least one scheme for the preparation and production of the non-toxic liquid solutions for biocidal application against pathogenic viruses; and b) using the scheme to prepare and produce specific formulated viral bacterial biocidal solutions comprising colloidal silver particles and ions in pure distilled aqueous water solution with less than 2 ppm of dissolved solids, wherein the colloidal silver particles are prepared using a voltage, the voltage is 26 volts DC or less, the colloidal silver particles have a particle size of between 0.3 nm and 0.6 nm, and either (i) the number of unattached pure silver particles and ions are from 200,000 to 2 million, or (ii) the concentration of unattached pure silver particles and ions is from 0.6 ppm to 6 ppm, the biocidal solutions thus made are effective to reduce or eliminate pathogenic viruses and/or retard the effects of pathogenic viruses.

5. A method of preparing and producing non-toxic liquid specific formulated biocidal substance solutions that can be used to reduce or eliminate pathogenic molds and/or retard the effects of pathogenic molds, the method comprising the steps of: a) creating at least one scheme for the preparation and production of the non-toxic liquid solutions for biocidal application against pathogenic molds; and b) using the scheme to prepare and produce specific formulated mold bacterial biocidal solutions comprising colloidal silver particles and ions in pure distilled aqueous water solution with less than 2 ppm of dissolved solids, wherein the colloidal silver particles are prepared using a voltage, the voltage is 26 volts DC or less, the colloidal silver particles have a particle size of between 0.5 nm and 0.7 nm, and either (i) the number of unattached pure silver particles and ions are from 200,000 to 2 million, or (ii) the concentration of unattached pure silver particles and ions is from 0.6 ppm to 6 ppm, the biocidal solutions thus made are effective to reduce or eliminate pathogenic molds and/or retard the effects of pathogenic molds.

6. A method of preparing and producing non-toxic liquid specific formulated biocidal substance solutions that can be used to reduce or eliminate pathogenic fungal growths and/or retard the effects of pathogenic fungal growths, the method comprising the steps of: a) creating at least one scheme for the preparation and production of the non-toxic liquid solutions for biocidal application against pathogenic fungal growths; and b) using the scheme to prepare and produce specific formulated fungal solutions comprising colloidal silver particles and ions in pure distilled aqueous water solution with less than 2 ppm of dissolved solids, wherein the colloidal silver particles are prepared using a voltage, the voltage is 26 volts DC or less, the colloidal silver particles have a particle size of between 0.5 nm and 0.7 nm, and either (i) the number of unattached pure silver particles and ions are from 200,000 to 2 million, or (ii) the concentration of unattached pure silver particles and ions is from 0.6 ppm to 6 ppm, the biocidal solutions thus made are effective to reduce or eliminate pathogenic fungal growths and/or retard the effects of pathogenic fungal growths.

* * * * *